US008008261B2

(12) United States Patent
Badley et al.

(10) Patent No.: US 8,008,261 B2
(45) Date of Patent: Aug. 30, 2011

(54) METHODS OF REDUCING TRAIL-INDUCED APOPTOSIS BY TRAIL ISOFORMS

(75) Inventors: Andrew D. Badley, Rochester, MN (US); Gary D. Bren, Chatfield, MN (US); David J. Schnepple, Crofton, MD (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 207 days.

(21) Appl. No.: 12/376,430

(22) PCT Filed: Aug. 2, 2007

(86) PCT No.: PCT/US2007/075115
§ 371 (c)(1),
(2), (4) Date: Feb. 4, 2009

(87) PCT Pub. No.: WO2008/088582
PCT Pub. Date: Jul. 24, 2008

(65) Prior Publication Data
US 2010/0172914 A1 Jul. 8, 2010

Related U.S. Application Data

(60) Provisional application No. 60/821,520, filed on Aug. 4, 2006.

(51) Int. Cl.
*A61K 38/17* (2006.01)
*C07K 14/705* (2006.01)
(52) U.S. Cl. ........................ 514/18.9; 514/21.2; 530/350
(58) Field of Classification Search .......................... None
See application file for complete search history.

(56) References Cited

U.S. PATENT DOCUMENTS

| 4,036,945 | A | 7/1977 | Haber |
| 4,331,647 | A | 5/1982 | Goldenberg |
| 5,763,223 | A | 6/1998 | Wiley et al. |
| 6,284,236 | B1 | 9/2001 | Wiley et al. |
| 6,521,228 | B1 | 2/2003 | Wiley et al. |
| 7,736,637 | B2 * | 6/2010 | Wiley et al. |
| 2002/0061525 | A1 | 5/2002 | Yelin et al. |

FOREIGN PATENT DOCUMENTS

| EP | 1666591 A1 | 6/2006 |
| WO | WO9111465 A1 | 8/1991 |
| WO | WO2004047871 A2 | 6/2004 |

OTHER PUBLICATIONS

Shah et al., In vivo imaging of S-TRAIL-mediated tumor regression and apoptosis, Mol. Ther. 11(6):926-931, Jun. 2005.*
Locksley et al., The TNF and TNF receptor superfamilies: Integrating mammalian biology, Cell, 104:487-501, Feb. 23, 2001.*
Yan et al., Two-amino acid molecular switch in an epithelial morphogen that regulates binding to tow distinct receptors, Science, 290(5491):523-527, Oct. 20, 2000.*
T.E. Creighton, PROTEINS: Structurs and Molecular Principles, (W.H. Freeman & Co.:New York), pp. 223-227, 1984.*
GenBank® accession No. NM_001101 dated Nov. 1, 2009.
GenBank® GI No. 112820323 dated Dec. 31, 2006, Accession DQ848564.
Almasan and Ashkenazi, "Apo2L/TRAIL: apoptosis signaling, biology, and potential for cancer therapy," Cytokine Growth Factor Rev., 2003, 14:337-348.
Baetu and Hiscott, "On the TRAIL to apoptosis," Cytokine Growth Factor Rev., 2002, 13:199-207.
Barbas and Lerner, "Combinatorial immunoglobulin libraries on the surface of phage (phabs): Rapid selection of antigen-specific Fabs," Methods: A Companion to Methods in Enzymology, 1991, 2(2):119-124.
Baines and Thorpe, "Purification of Immunoglobulin G (IgG)," Meth. Mol. Biol., 1992, 10:79-104.
Carter et al., "Humanization of an anti-p185HER2 antibody for human cancer therapy," Proc. Natl. Acad. Sci. USA, 1992, 89:4285-4289.
Coligan et al., "Production of Polyclonal Antisera in Rabbits, Rats, Mice and Hamsters," Current Protocols in Immunology, 1992, section 2.4.1.
Cretney et al., "TNF-related apoptosis-inducing ligand as a therapeutic agent in autoimmunity and cancer," Immunol Cell Biol, 2006, 84:87-98.
Edelman et al., "Hydrolysis with Pepsin," Meth. Enzymol., 1967, 1:422.
Emery et al., "Osteoprotegerin Is a Receptor for the Cytotoxic Ligand TRAIL," J. Biol. Chem., 1998, 273:14363-14377.
Green et al., "Antigen-specific human monoclonal antibodies from mice engineered with human Ig heavy and light chain YACs," Nature Genet., 1994, 7:13-21.
Green et al., "Production of Polyclonal Antisera," Immunochemical Protocols, 1992, 10:1-5, Manson (ed.), Humana Press.
Held and Schulze-Osthoff, "Potential and caveats of TRAIL in cancer therapy," Drug Resistance Updates, 2001, 4:243-252.
Holen et al., "Osteoprotegerin (OPG) is a survival factor for human prostate cancer cells," Cancer Res., 2002, 62:1619-1623.
Hu et al., "Tumor Necrosis Factor-related Apoptosis-inducing Ligand Receptors Signal NF-κB and JNK Activation and Apoptosis through Distinct Pathways," J Biol Chem, 1999, 274(43):30603-30610.
Hyrup et al., "Peptide Nucleic Acids (PNA): Synthesis, Properties and Potential Applications," Bioorg. Med. Chem., 1996, 4:5-23.
Jones et al., "Replacing the complementarity-determining regions in a human antibody with those from a mouse," Nature, 1986, 321(6069):522-525.
Köhler and Milstein, "Continuous cultures of fused cells secreting antibody of predefined specificity," Nature, 1975, 256:495-497.

(Continued)

*Primary Examiner* — Lorraine Spector
*Assistant Examiner* — Claire Kaufman
(74) *Attorney, Agent, or Firm* — Fish & Richardson P.C.

(57) ABSTRACT

This document provides to methods and materials related to apoptosis. For example, methods and materials for modulating apoptosis are provided. In addition, methods and materials for treating a mammal having an apoptosis-associated condition are provided.

2 Claims, 19 Drawing Sheets

OTHER PUBLICATIONS

Krieg et al., "Trail-β and Trail-γ: two novel splice variants of the human TNF-related apoptosis-inducing ligand (TRAIL) without apoptotic potential," Br J Cancer, 2003, 88(6):918-927.

Leblanc and Ashkenazi, "Apo2L/TRAIL and its death and decoy receptors," Cell Death Differ, 2003, 10:66-75.

Lonberg et al., "Antigen-specific human antibodies from mice comprising four distinct genetic modifications," Nature, 1994, 368(6474):856-859.

Losman et al., "Baboon anti-idiotype antibodies mimic a carcinoembryonic antigen epitope," Int. J. Cancer, 1990, 46 (2):310-314.

Lum et al., "Induction of Cell Death in Human Immunodeficiency Virus-Infected Macrophages and Resting Memory CD4 T Cells by TRAIL/Apo2L," J. Virol., 2001, 75(22):11128-11136.

Malhi and Gores, "TRAIL resistance results in cancer progression: a TRAIL to perdition?" Oncogene, 2006, 25 (56):7333-7335.

Nisonoff et al., "Separation of univalent fragments from the bivalent rabbit antibody molecule by reduction of disulfide bonds," Arch. Biochem. Biophys., 1960, 89:230-244.

Orlandi et al., "Cloning immunoglobulin variable domains for expression by the polymerase chain reaction," Proc. Natl. Acad. Sci. USA, 1989, 86:3833-3837.

Porter, "The hydrolysis of rabbit g-globulin and antibodies with crystalline papain," Biochem. J., 1959, 73:119-127.

Riechmann et al., "Reshaping human antibodies for therapy," Nature, 1988, 332:323-327.

Sambrook et al., Molecular Cloning, second edition, sections 7.39-7.52 Cold Spring harbor Laboratory, Plainview, NY.

Sandhu, "Protein engineering of antibodies," Crit. Rev. Biotech., 1992, 12(5-6):437-462.

Singer et al., "Optimal humanization of 1B4, an anti-CD18 murine monoclonal antibody, is achieved by correct choice of human V-region framework sequences," J. Immunol., 1993, 150:2844-2857.

Summerton and Weller, "Morpholino antisense oligomers: design, preparation, and properties," Antisense Nucleic Acid Drug Dev., 1997, 7:187-195.

Taylor et al., "Human immunoglobulin transgenes undergo rearrangement, somatic mutation and class switching in mice that lack endogenous IgM," Int. Immunol., 1994, 6(4):579-591.

Van Loon and Weinshilboum, "Thiopurine methyltransferase isozymes in human renal tissue," Drug Metab. Dispos., 1990, 18:632-638.

Van Loon et al., "Human kidney thiopurine methyltransferase: Photoaffinity labeling with S-adenosyl-L-methionine," Biochem Pharmacol., 1992, 44:775-785.

Verhoeyen et al., "Reshaping human antibodies: grafting an antilysozyme activity," Science, 1988, 239:1534-1536.

Vlahakis et al., "Human Immunodeficiency Virus-Induced Apoptosis of Human Hepatocytes via CXCR4," J. Infect. Dis., 2003, 188(10):1455-1460.

Wang and El-Deiry, "Requirement of p53 targets in chemosensitization of colonic carcinoma to death ligand therapy," Proc Natl Acad Sci USA, 2003, 100(25):15095-15100.

Winter et al., "Making antibodies by phage display technology," Ann. Rev. Immunol., 1994, 12:433-455.

Wong et al., "Human GM-CSF: molecular cloning of the complementary DNA and purification of the natural and recombinant proteins," Science, 1985, 228:810-815.

International Search Report/Written Opinion in PCT/US2007/75115 mailed Sep. 30, 2008, 12 pages.

International Preliminary Report on Patentability in PCT/US2007/75115 mailed Feb. 10, 2009, 8 pages.

Wang and El-Deiry, "TRAIL and apoptosis induction by TNF-family death receptors," Oncogene, 2003, 22:8628-8633.

* cited by examiner

```
1   M  A  M  M  E  V  Q  G  G  P  S  L  G  Q  T  C  V  L  I  V
1   ATGGCTATGATGGAGGTCCAGGGGGGACCCAGCCTGGGACAGACCTGCGTGCTGATCGTG
21  I  F  T  V  L  L  Q  S  L  C  V  A  V  T  Y  V  Y  F  T  N
61  ATCTTCACAGTGCTCCTGCAGTCTCTCTGTGTGGCTGTAACTTACGTGTACTTTACCAAC
41  E  L  K  Q  M  Q  D  K  Y  S  K  S  G  I  A  C  F  L  K  E
121 GAGCTGAAGCAGATGCAGGACAAGTACTCCAAAAGTGGCATTGCTTGTTTCTTAAAAGAA
61  D  D  S  Y  W  D  P  N  D  E  E  S  M  N  S  P  C  W  Q  V
181 GATGACAGTTATTGGGACCCCAATGACGAAGAGAGTATGAACAGCCCCTGCTGGCAAGTC
81  K  W  Q  L  R  Q  L  V  R  K  T  P  R  M  K  R  L  W  A  A
241 AAGTGGCAACTCCGTCAGCTCGTTAGAAAGACTCCAAGAATGAAAAGGCTCTGGGCCGCA
101 K  *                                          (SEQ ID NO:1)
301 AAATAA                                         (SEQ ID NO:4)
```

Figure 7

```
1    T  P  R  M  K  R  L  W  A  A  K  *         (SEQ ID NO:2)
1    ACTCCAAGAATGAAAAGGCTCTGGGCCGCAAAATAA        (SEQ ID NO:5)
```

Figure 8

```
1     TTTCATTTCC TCACTGACTA TAAAAGAATA GAGAAGGAAG GGCTTCAGTG ACCGGCTGCC
61    TGGCTGACTT ACAGCAGTCA GACTCTGACA GGATCATGGC TATGATGGAG GTCCAGGGGG
121   GACCCAGCCT GGGACAGACC TGCGTGCTGA TCGTGATCTT CACAGTGCTC CTGCAGTCTC
181   TCTGTGTGGC TGTAACTTAC GTGTACTTTA CCAACGAGCT GAAGCAGATG CAGGACAAGT
241   ACTCCAAAAG TGGCATTGCT TGTTTCTTAA AAGAAGATGA CAGTTATTGG GACCCCAATG
301   ACGAAGAGAG TATGAACAGC CCTGCTGGC AAGTCAAGTG GCAACTCCGT CAGCTCGTTA
361   GAAAGATGAT TTTGAGAACC TCTGAGGAAA CCATTTCTAC AGTTCAAGAA AAGCAACAAA
421   ATATTTCTCC CCTAGTGAGA GAAAGAGGTC CTCAGAGAGT AGCAGCTCAC ATAACTGGGA
481   CCAGAGGAAG AAGCAACACA TTGTCTTCTC CAAACTCCAA GAATGAAAAG GCTCTGGGCC
541   GCAAAATAAA CTCCTGGGAA TCATCAAGGA GTGGGCATTC ATTCCTGAGC AACTTGCACT
601   TGAGGAATGG TGAACTGGTC ATCCATGAAA AAGGGTTTTA CTACATCTAT TCCCAAACAT
661   ACTTTCGATT TCAGGAGGAA ATAAAAGAAA ACACAAAGAA CGACAAACAA ATGGTCCAAT
721   ATATTTACAA ATACACAAGT TATCCTGACC CTATATTGTT GATGAAAAGT GCTAGAAATA
781   GTTGTTGGTC TAAAGATGCA GAATATGGAC TCTATTCCAT CTATCAAGGG GGAATATTTG
841   AGCTTAAGGA AAATGACAGA ATTTTTGTTT CTGTAACAAA TGAGCACTTG ATAGACATGG
901   ACCATGAAGC CAGTTTTTTC GGGGCCTTTT TAGTTGGCTA ACTGACCTGG AAAGAAAAAG
961   CAATAACCTC AAAGTGACTA TTCAGTTTTC AGGATGATAC ACTATGAAGA TGTTTCAAAA
1021  AATCTGACCA AAACAAACAA ACAGAAAACA GAAAACAAAA AAACCTCTAT GCAATCTGAG
1081  TAGAGCAGCC ACAACCAAAA AATTCTACAA CACACACTGT TCTGAAAGTG ACTCACTTAT
1141  CCCAAGAGAA TGAAATTGCT GAAAGATCTT TCAGGACTCT ACCTCATATC AGTTTGCTAG
1201  CAGAAATCTA GAAGACTGTC AGCTTCCAAA CATTAATGCA ATGGTTAACA TCTTCTGTCT
1261  TTATAATCTA CTCCTTGTAA AGACTGTAGA AGAAAGAGCA ACAATCCATC TCTCAAGTAG
1321  TGTATCACAG TAGTAGCCTC CAGGTTTCCT TAAGGGACAA CATCCTTAAG TCAAAAGAGA
1381  GAAGAGGCAC CACTAAAAGA TCGCAGTTTG CCTGGTGCAG TGGCTCACAC CTGTAATCCC
1441  AACATTTGG GAACCCAAGG TGGGTAGATC ACGAGATCAA GAGATCAAGA CCATAGTGAC
1501  CAACATAGTG AAACCCCATC TCTACTGAAA GTACAAAAAT TAGCTGGGTG TGTTGGCACA
1561  TGCCTGTAGT CCCAGCTACT TGAGAGGCTG AGGCAAGAGA ATTGTTTGAA CCCGGGAGGC
1621  AGAGGTTGCA GTGTGGTGAG ATCATGCCAC TACACTCCAG CCTGGCGACA GAGCGAGACT
1681  TGGTTTCAAA AAAAAAAAAA AAAAAAACTT CAGTAAGTAC GTGTTATTTT TTCAATAAA
1741  ATTCTATTAC AGTATGTCAA AAAAAAAAAA AAAAAA      (SEQ ID NO:3)
```

Figure 9

METHODS OF REDUCING TRAIL-INDUCED APOPTOSIS BY TRAIL ISOFORMS

CROSS-REFERENCE TO RELATED APPLICATIONS

This Application is a National Stage application under 35 U.S.C. 371 and claims the benefit under 35 U.S.C. 119(a) of International Application No. PCT/US2007/075115 having an International Filing Date of Aug. 2, 2007, which claims priority of U.S. Provisional Application Ser. No. 60/821,520, having a filing date of Aug. 4, 2006.

STATEMENT AS TO FEDERALLY SPONSORED RESEARCH

This invention was made with government support under AI 062261 awarded by National Institutes of Health. The government has certain rights in the invention.

BACKGROUND

1. Technical Field

This document relates to methods and materials involved in apoptosis, apoptosis inhibitors, and to modulating the activity of TRAIL.

2. Background Information

Apoptosis is a normal physiologic process leading to cell death that can be induced by normal processes as well as several pathological conditions and injuries. Apoptosis can be involved in conditions including, but not limited to, cardiovascular disease, cancer, immunoregulation, viral diseases (e.g., HIV infection), anemia, neurological disorders, gastrointestinal disorders, diabetes, hair loss, rejection of organ transplants, prostate hypertrophy, obesity, ocular disorders, stress, and aging.

TNF related apoptosis inducing ligand (TRAIL) is a member of the tumor necrosis factor (TNF) superfamily of death-inducing ligands whose members include Fas ligand and TNF. Ligation of TRAIL to its cognate receptors can cause cell death by apoptosis or may cause NF-κB activation (Hu, et al., *J. Biol. Chem.*, 274:30603-10 (1999)). There are three known TRAIL isoforms (TRAILα, TRAILβ, and TRAILγ). TRAIL has widespread expression on multiple cell lineages and has shown potent toxicity for many tumors and virally infected cells, while sparing most healthy cells (Held, et al., *Drug Resist. Updat.*, 4:243-52 (2001); Baetu and Hiscott, *Cytokine Growth Factor*, 13:199-207 (2002)). TRAIL mediates cell death via binding of one of five TRAIL receptors (e.g., TRAIL-R1, -R2, -R3, -R4, and osteoprotegerin (OPG)). TRAIL-R1 and -R2 can cause an apoptotic signal, while TRAIL-R3 and -R4 lack intracellular regions that can propagate an apoptotic signal (Wang and El-Deiry, *Oncogene*, 22:8628-33 (2003)).

OPG, a soluble inhibitor of RANK ligand, also binds to TRAIL in humans, and can be a soluble decoy receptor for TRAIL (Emery, et al., *J. Biol. Chem.*, 273:14363-7 (1998); Holen, et al., *Cancer Res.*, 62:1619-23 (2002)). Expression of TRAIL-R1, TRAIL-R2, or TRAIL-R1 and TRAIL-R2 on a cell is required to induce TRAIL-mediated apoptosis of that cell. However, TRAIL-R1 and/or -R2 receptor expression alone is insufficient to render a cell susceptible to TRAIL-mediated cell death. TRAIL agonists are in pre-clinical development for used as therapy for human tumors because of their selective induction of cell death in transformed and virally infected cells.

SUMMARY

This document relates to methods and materials related to apoptosis and apoptosis inhibitors. The methods and materials provided herein are based, in part, on the discovery of a TNF related apoptosis inducing ligand (TRAIL) isoform, TRAIL short (TRAIL-s), that can inhibit TRAIL-mediated cell death (e.g., apoptosis).

In general, one aspect of this document features a substantially pure polypeptide having TRAIL-s activity. The polypeptide can comprise, or consist essentially of, the amino acid sequence set forth in SEQ ID NO:1. The polypeptide can comprise, or consist essentially of, an amino acid sequence having 80% identity to the sequence set forth in SEQ ID NO:1. The polypeptide can comprise, or consist essentially of, the amino acid sequence set forth in SEQ ID NO:2. The polypeptide can comprise, or consist essentially of, an amino acid sequence having 80% identity to the sequence set forth in SEQ ID NO:2.

In another aspect, this document features an isolated nucleic acid comprising, or consisting essentially of, a nucleic acid sequence that encodes a polypeptide having TRAIL-s activity. The polypeptide can comprise, or consist essentially of, the amino acid sequence set forth in SEQ ID NO:1. The polypeptide can comprise, or consist essentially of, an amino acid sequence having 80% identity to the sequence set forth in SEQ ID NO:1. The polypeptide can comprise, or consist essentially of, the amino acid sequence set forth in SEQ ID NO:2. The polypeptide can comprise, or consist essentially of, an amino acid sequence having fewer than 5 mismatches as compared to the sequence set forth in SEQ ID NO:2. The nucleic acid can hybridize under highly stringent hybridization conditions to the nucleic acid sequence set forth in SEQ ID NO:3 and does not contain exon 4. The nucleic acid can hybridize under highly stringent hybridization conditions to the nucleic acid sequence set forth in SEQ ID NO:4 and does not contain exon 4. The nucleic acid can hybridize under highly stringent hybridization conditions to the nucleic acid sequence set forth in SEQ ID NO:5 and does not contain exon 4.

In another aspect, this document features a purified antibody having the ability to bind to a polypeptide having TRAIL-s activity to a level greater than the level of binding to a TRAILα, TRAILβ, or TRAILγ polypeptide. The antibody can have a dissociation constant that is less than $10^{-7}$ for the polypeptide having TRAIL-s activity. The polypeptide having TRAIL-s activity can be a human TRAIL-s polypeptide. The polypeptide having TRAIL-s activity can be a polypeptide having the sequence set forth in SEQ ID NO:1. The polypeptide having TRAIL-s activity can be a polypeptide having the sequence set forth in SEQ ID NO:2. The antibody can have no detectable binding to a TRAILα, TRAILβ, or TRAILγ polypeptide. The antibody can have a dissociation constant that is greater than $10^{-6}$ for binding a TRAILα, TRAILβ, or TRAILγ polypeptide. The antibody can inhibit the binding of the polypeptide having TRAIL-s activity to its receptor.

In another aspect, this document features a method for treating a mammal having an apoptosis-associated condition. The method comprises, or consists essentially of, administering to the mammal a substantially pure polypeptide having TRAIL-s activity.

In another aspect, this document features a method for treating a mammal having an apoptosis-associated condition. The method comprises, or consists essentially of, administering to the mammal a TRAIL-s antagonist. The TRAIL-s antagonist can be an antibody having the ability to bind to a polypeptide having TRAIL-s activity.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 7. Nucleic acid (SEQ ID NO:4) and amino acid (SEQ ID NO:1) sequences of TRAIL-s. The splice junction between exon 2 and exon 5 is bold and underlined. The asterisk indicates a stop codon.

FIG. 8. Nucleic acid (SEQ ID NO:5) and amino acid (SEQ ID NO:2) sequences of the TRAIL-s C-terminus. The asterisk indicates a stop codon.

FIG. 9. Annotated TRAIL mRNA sequence (SEQ ID NO:3). The open reading frame is from nucleotide 96 to 941, with exon 1=nt 96 to 227, exon 2=nt 228 to 365, exon 3=nt 366 to 408, exon 4=nt 409 to 513, and exon 5=nt 514 to 941.

DETAILED DESCRIPTION

Figure 1:
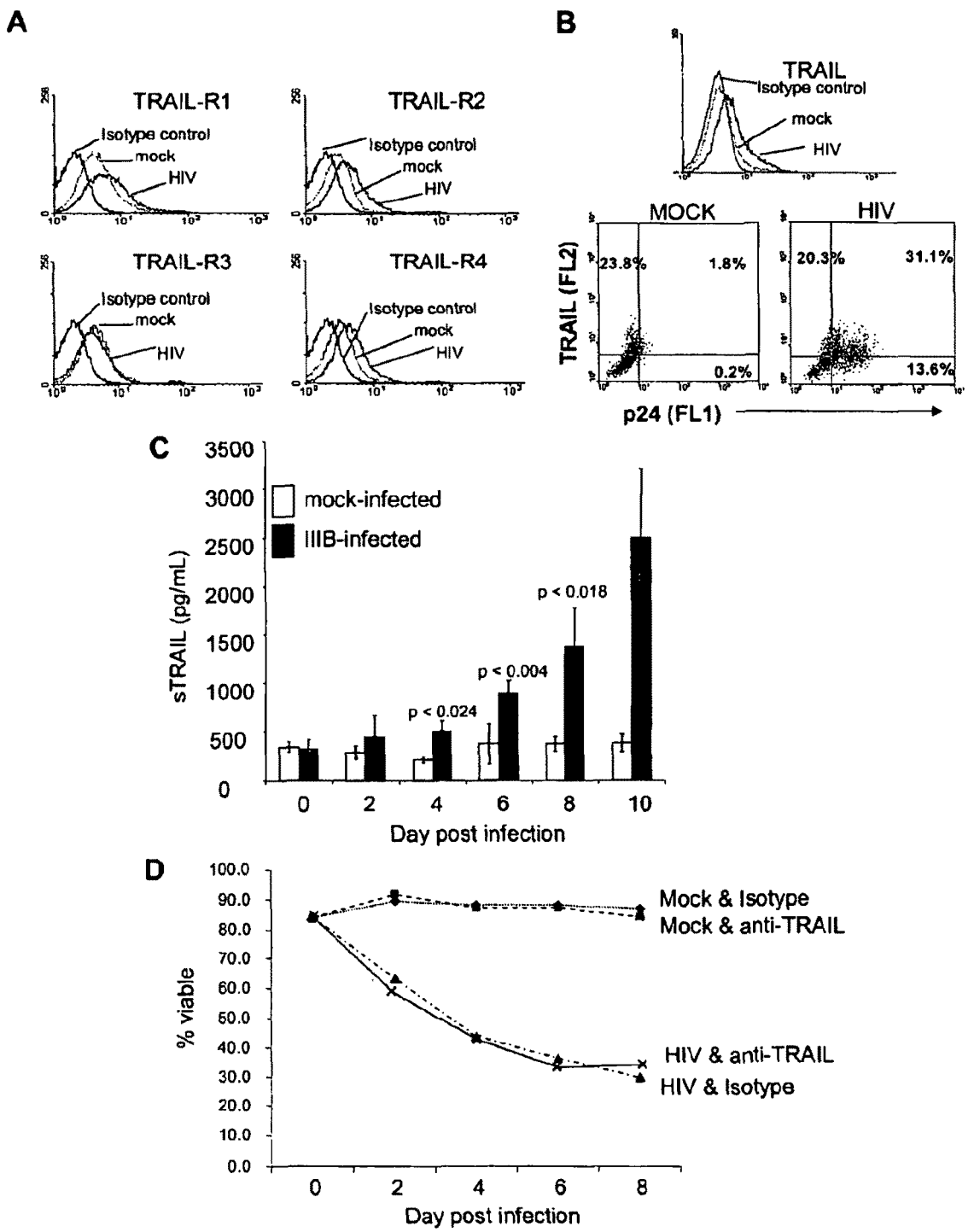
FIG. 1. (A) TRAIL receptor expression in peripheral blood lymphocytes (PBLs) infected with HIV. (B) Cell-associated and (C) soluble TRAIL expression in PBLs infected with HIV. The results shown are the means of four infections, ±s.e.m. (D) Effect of anti-TRAIL antibody on cell viability in PBLs infected with HIV. The data are representative of three separate replicates. (E) Cell-associated TRAIL expression in PBLs from HIV-negative donors that were infected in vitro with HIV-1 (IIIB) or mock-infected and analyzed four days later (the results are representative of four independent experiments).
Figure 1:
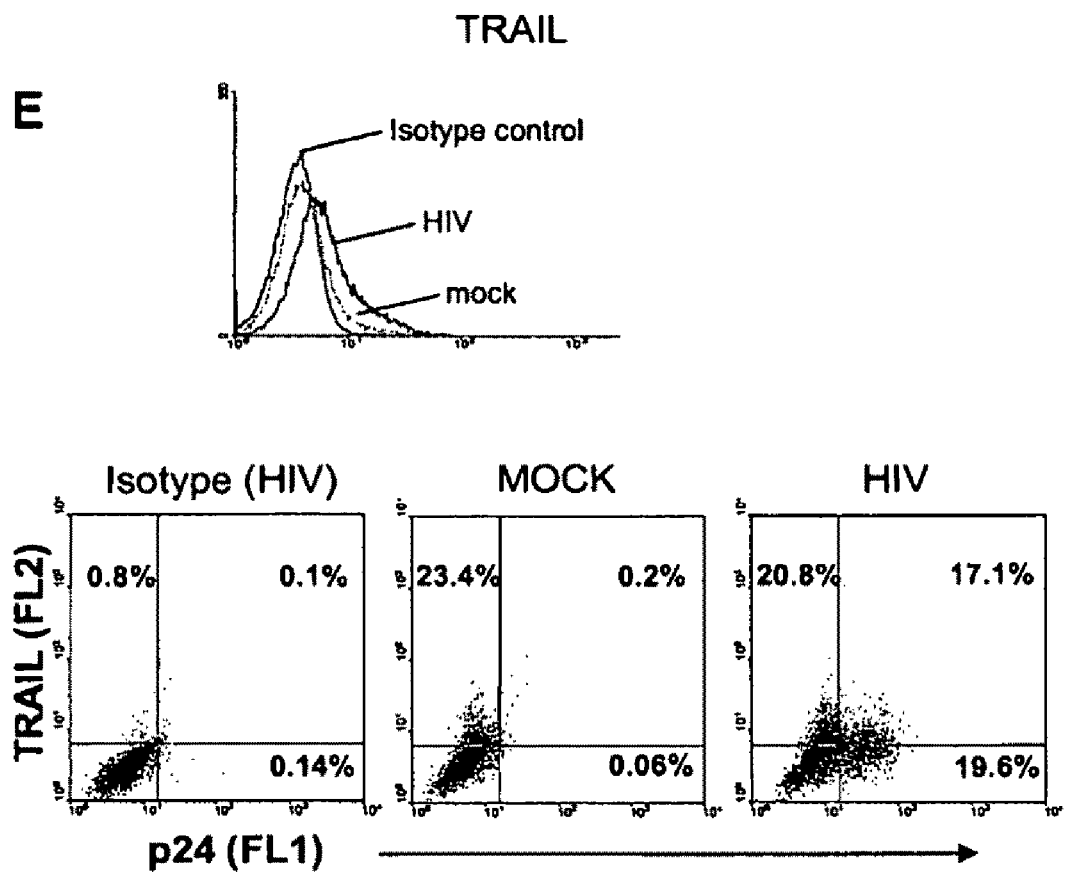

This document provides methods and materials related to apoptosis and apoptosis inhibitors. For example, this document provides substantially pure polypeptides having TRAIL short (TRAIL-s) activity and isolated nucleic acids encoding polypeptides having TRAIL-s activity. This document also provides methods and materials for making and using an antibody that can bind a polypeptide having TRAIL-s activity and not to a TRAILα, TRAILβ, or TRAILγ polypeptide. This document also provides methods and materials for treating a mammal having an apoptosis-associated condition.

Polypeptides Having TRAIL-s Activity and Nucleic Acids Encoding Polypeptides Having TRAIL-s Activity This document provides a substantially pure polypeptide having TRAIL-s activity. As used herein, a "polypeptide having TRAIL-s activity" is a polypeptide having the ability to compete with TRAIL for TRAIL receptor binding and inhibit TRAIL-mediated cell death (e.g., apoptosis). The term "substantially pure" with respect to a polypeptide refers to a polypeptide that has been separated from cellular components with which it is naturally accompanied. Typically, a polypeptide having TRAIL-s activity is substantially pure when it is at least 60 percent (e.g., 65, 70, 75, 80, 90, 95, or 99 percent), by weight, free from proteins and naturally-occurring organic molecules with which it is naturally associated. In general, a substantially pure polypeptide will yield a single major band on a non-reducing polyacrylamide gel.

The polypeptides provided herein can be at least five amino acids in length (e.g., at least 6, 7, 10, 15, 30, 50, 70, or 100 amino acids).

A substantially pure polypeptide having TRAIL-s activity can be a polypeptide having a sequence that is at least 70 percent identical to SEQ ID NO:1 or SEQ ID NO:2. For example, a polypeptide having TRAIL-s activity can have at least 75, 80, 85, 90, 95, 98, or 99 percent identity to SEQ ID NO:1 or SEQ ID NO:2. In some cases, a polypeptide having TRAIL-s activity can have the exact amino acid sequence set forth in SEQ ID NO:1 or SEQ ID NO:2.

The percent identity between a particular amino acid sequence and the amino acid sequence set forth in SEQ ID NO:1 or SEQ ID NO:2 is determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., "www" dot "fr" dot "com" slash "blast" slash) or the State University of New York-Old Westbury Library (call number: QH 447.M6714). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical amino acid residue is presented in both sequences. The percent identity is determined by dividing the number of matches by the length of the full-length amino acid sequence set forth in SEQ ID NO:1 or SEQ ID NO:2 followed by multiplying the resulting value by 100. For example, an amino acid sequence that has 98 matches when aligned with the sequence set forth in SEQ ID NO:1 is 97.0 percent identical to the sequence set forth in SEQ ID NO:1 (i.e., 98÷101*100=97.0).

It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

In some cases, a substantially pure polypeptide having TRAIL-s activity can have fewer than 10 (e.g., fewer than 9, 8, 7, 6, 5, 4, 3, or 2) mismatches as compared to SEQ ID NO:2. For example, a polypeptide having TRAIL-s activity can have 4, 3, 2, or 1 mismatches as compared to SEQ ID NO:2. In some cases, a polypeptide having TRAIL-s activity can have the exact amino acid sequence set forth in SEQ ID NO:2.

The number of mismatches between a particular amino acid sequence and SEQ ID NO:2 is determined as follows. First, the amino acid sequences are aligned using the BLAST 2 Sequences (Bl2seq) program from the stand-alone version of BLASTZ containing BLASTP version 2.0.14 as described herein.

Once aligned, the number of mismatches is determined by counting the number of positions where an identical amino acid residue is not presented in both sequences.

A substantially pure polypeptide having TRAIL-s activity can be obtained, for example, by extraction from a natural source (e.g., lymphocytes), chemical synthesis, or by recombinant production in a host cell. To recombinantly produce a polypeptide having TRAIL-s activity, a nucleic acid sequence encoding a polypeptide having TRAIL-s activity can be ligated into an expression vector and used to transform a bacterial or eukaryotic host cell (e.g., insect, yeast, or mammalian cells). In general, nucleic acid constructs can include a regulatory sequence operably linked to a nucleic acid sequence encoding a polypeptide having TRAIL-s activity. Regulatory sequences do not typically encode a gene product, but instead affect the expression of the nucleic acid sequence. In bacterial systems, a strain of *Escherichia coli* such as BL-21 can be used. Suitable *E. coli* vectors include the pGEX series of vectors (Amersham Biosciences Corp., Piscataway, N.J.) that produce fusion proteins with glutathione S-transferase (GST). Transformed *E. coli* typically are grown exponentially, and then stimulated with isopropylthiogalactopyranoside (IPTG) prior to harvesting. In general, such fusion proteins can be soluble and can be purified from lysed cells by adsorption to glutathione-agarose beads followed by elution in the presence of free glutathione. The pGEX vectors can be designed to include thrombin or factor Xa protease cleavage sites so that the cloned target gene product can be released from the GST moiety.

In eukaryotic host cells, a number of viral-based expression systems can be utilized to express polypeptides having TRAIL-s activity. A nucleic acid encoding a polypeptide having TRAIL-s activity can be cloned into, for example, a baculoviral vector such as pBlueBac (Invitrogen, Carlsbad, Calif.) and then used to co-transfect insect cells such as *Spodoptera frugiperda* (Sf9) cells with wild type DNA from *Autographa californica* multiply enveloped nuclear polyhedrosis virus (AcMNPV). Recombinant viruses producing polypeptides provided herein can be identified by standard methodology. In some cases, a nucleic acid encoding a polypeptide having TRAIL-s activity can be introduced into a SV40, retroviral, or vaccinia based viral vector and used to infect suitable host cells.

Mammalian cell lines that stably express polypeptides having TRAIL-s activity can be produced using expression vectors with the appropriate control elements and a selectable marker. For example, the eukaryotic expression vectors pCR3.1 (Invitrogen) and p91023(B) (see Wong et al., *Science*, 228:810-815 (1985)) can be used to express a polypeptide having TRAIL-s activity in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of the expression vector by electroporation, lipofection, calcium phosphate or calcium chloride co-precipitation, DEAE dextran, or other suitable transfection method, stable cell lines can be selected, e.g., by antibiotic resistance to G418, kanamycin, or hygromycin. In some cases, amplified sequences can be ligated into a mammalian expression vector such as pcDNA3 (Invitrogen) and then transcribed and translated in vitro using wheat germ extract or rabbit reticulocyte lysate.

Polypeptides having TRAIL-s activity can be purified by known chromatographic methods including DEAE ion exchange, gel filtration, and hydroxylapatite chromatography. See, e.g., Van Loon and Weinshilboum, *Drug Metab. Dispos.*, 18:632-638 (1990); and Van Loon et al., *Biochem. Pharmacol.*, 44:775-785 (1992). Polypeptides having TRAIL-s activity can be modified to contain an amino acid sequence that allows the polypeptide to be captured onto an affinity matrix. For example, a tag such as c-myc, hemagglutinin, polyhistidine, or Flag™ (Kodak) can be used to aid polypeptide purification. Such tags can be inserted anywhere within a polypeptide including at either the carboxyl or amino terminus. Other fusions that can be useful include enzymes that aid in the detection of a polypeptide, such as alkaline phosphatase. Immunoaffinity chromatography also can be used to purify polypeptides having TRAIL-s activity.

In some cases, a polypeptide having TRAIL-s activity can be a polypeptide that is covalently attached to oligomers, such as short, amphiphilic oligomers that enable oral administration or improve the pharmacokinetic or pharmacodynamic profile of the conjugated polypeptide. The oligomers can comprise water soluble polyethylene glycol (PEG) and lipid soluble alkyls (short chain fatty acid polymers). See, for example, International Patent Application Publication No. WO 2004/047871. In some cases, a polypeptide having TRAIL-s activity can be a polypeptide that is fused to the Fc domain of an immunoglobulin molecule (e.g., an IgG1 molecule) such that active transport of the fusion polypeptide across epithelial cell barriers via the Fc receptor occurs.

The polypeptides provided herein can contain the entire amino acid sequence set forth in SEQ ID NO:1 or SEQ ID NO:2. In some cases, a polypeptide can contain the amino acid sequence set forth in SEQ ID NO:1 or SEQ ID NO:2 except that the amino acid sequence contains one or between one and ten (e.g., between one and nine, between one and eight, between one and seven, between one and six, between one and five, between one and four, between one and three, or between one and two) amino acid residue additions, subtractions, and substitutions. For example, a polypeptide can contain the amino acid sequence set forth in SEQ ID NO:1 with one, two, three, four, five, six, seven, eight, nine, or ten single amino acid residue additions, subtractions, or substitutions. An example of such a polypeptide includes, without limitation, a polypeptide having the amino acid sequence set forth in SEQ ID NO:1 where the amino acid residue at position 43 is replaced with an arginine residue, the amino acid residue at position 85 is replaced with a lysine residue, and/or the amino acid residue at position 81 is replaced with a histidine residue. In some cases, a polypeptide can contain the amino acid sequence set forth in SEQ ID NO:2 with one, two, three, or four amino acid residue additions, subtractions, or substitutions. An example of such a polypeptide includes, without limitation, a polypeptide having the amino acid sequence set forth in SEQ ID NO:2 where the amino acid residue at position three is replaced with a lysine residue. Another example can be a polypeptide having the amino acid sequence set forth in SEQ ID NO:2 where the amino acid residue at position five is replaced with a histidine residue. Another example can be a polypeptide having the amino acid sequence set forth in SEQ ID NO:2 where the amino acid residue at position six is replaced with a lysine residue. Yet another example can be a polypeptide having the amino acid sequence set forth in SEQ ID NO:2 where the amino acid residue at position eleven is replaced with an arginine residue.

Any amino acid residue set forth in SEQ ID NO:1 or SEQ ID NO:2 can be subtracted, and any amino acid residue (e.g., any of the 20 conventional amino acid residues or any other type of amino acid such as ornithine or citrulline) can be added to the sequence set forth in SEQ ID NO:1 or SEQ ID NO:2. In some cases, a polypeptide provided herein can contain chemical structures such as ε-aminohcxanoic acid; hydroxylated amino acids such as 3-hydroxyproline, 4-hydroxyproline, (5R)-5-hydroxy-L-lysine, allo-hydroxylysine, and 5-hydroxy-L-norvaline; or glycosylated amino acids such as amino acids containing monosaccharides (e.g., D-glucose, D-galactose, D-mannose, D-glucosamine, and D-galactosamine) or combinations of monosaccharides.

Polypeptides having one or more amino acid substitutions relative to a native polypeptide can be prepared and modified as described herein. Amino acid substitutions can be conservative or non-conservative amino acid substitutions. Conservative amino acid substitutions include, for example, substitution of an acidic amino acid residue (e.g., aspartic acid or glutamic acid) with another acidic amino acid residue, substitution of a basic amino acid residue (e.g., lysine, arginine, or histidine) with another basic amino acid residue, substitution of a hydrophobic amino acid residue with another hydrophobic amino acid residue (e.g., substitution of leucine with isoleucine, methionine with valine, or alanine with valine), and substitution of a hydrophilic amino acid residue (e.g., serine, glycine, or threonine) with another hydrophilic amino acid residue.

Conservative amino acid substitutions also include substitution of an amino acid residue having a particular type of side chain with another amino acid residue having a similar type of side chain. For example, conservative amino acid substitutions include substitution of an amino acid residue having an aliphatic side chain (e.g., glycine, alanine, valine, leucine, or isoleucine) with another amino acid residue having an aliphatic side chain, substitution of an amino acid residue having an aliphatic-hydroxyl side chain (e.g., serine or threonine) with another amino acid residue having an aliphatic-hydroxyl side chain, substitution of an amino acid residue having an amide-containing side chain (e.g., asparagine or glutamine) with another amino acid residue having an amide-containing side chain, substitution of an amino acid residue having an aromatic side chain (e.g., phenylalanine, tyrosine, or tryptophan) with another amino acid residue having an aromatic side chain, substitution of an amino acid residue having a basic side chain (e.g., lysine, arginine, or histidine) with another amino acid residue having a basic side chain, and substitution of an amino acid residue having a sulfur-containing side chain (e.g., cysteine or methionine) with another amino acid residue having a sulfur-containing side chain.

A polypeptide having TRAIL-s activity can bind a TRAIL receptor (e.g., TRAIL-R1, -R2, -R3, -R4, or osteoprotegerin (OPG)). A substantially pure polypeptide having TRAIL-s activity can inhibit TRAIL-induced apoptosis in cells having a TRAIL receptor. Cells having a TRAIL receptor can be of any lineage. For example, cells having a TRAIL receptor include, without limitation, lymphocytes, neural cells, hepatocytes, myocytes, osteoblasts, and chondrocytes. Cells having a TRAIL receptor can be normal or abnormal (e.g., virally or bacterially infected, or malignant).

Any suitable method, such as PCR, can be used to obtain an isolated nucleic acid encoding a polypeptide having TRAIL-s activity. For example, the methods provided in the Example section can be used to obtain a nucleic acid encoding a polypeptide having TRAIL-s activity. As used herein, "isolated nucleic acid" refers to a nucleic acid that is separated from other nucleic acids that are present in a mammalian genome, including nucleic acids that normally flank one or both sides of the nucleic acid in a mammalian genome (e.g., nucleic acids that encode non-TRAIL polypeptides). The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

A nucleic acid provided herein can be at least about ten nucleotides in length. For example, the nucleic acid can be about 10, 11, 15-20 (e.g., 11, 12, 13, 14, 15, 16, 17, 18, 19, or 20 nucleotides in length), 20-50, 50-100 or greater than 100 nucleotides in length (e.g., greater than 150, 200, 250, 300, 350, 400, 450, 500, 750, or 1000 nucleotides in length). Nucleic acids provided herein can be in a sense or antisense orientation, can be identical or complementary to the sequence set forth in SEQ ID NO:3, SEQ ID NO:4, or SEQ ID NO:5, and can be DNA, RNA, or nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller, *Antisense Nucleic Acid Drug Dev.*, 7:187-195 (1997); and Hyrup, et al., *Bioorgan. Med. Chem.*, 4:5-23 (1996). In addition, the deoxyphosphate backbone can be replaced with, for example, a phosphorothioate or phosphorothioate backbone, a phosphoroamidite, or an alkyl phosphotriester backbone.

Nucleic acids provided herein can hybridize, under hybridization conditions, to the sense or antisense strand of a nucleic acid having the sequence set forth in SEQ ID NO:3, SEQ ID NO:4, or SEQ ID NO:5. The hybridization conditions can be moderately or highly stringent hybridization conditions.

As used herein, moderately stringent hybridization conditions mean the hybridization is performed at about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 50° C. with a wash solution containing 2×SSC and 0.1% sodium dodecyl sulfate.

Highly stringent hybridization conditions mean the hybridization is performed at about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 65° C. with a wash solution containing 0.2×SSC and 0.1% sodium dodecyl sulfate.

Hybridization can be done by Southern or Northern analysis to identify a DNA or RNA sequence, respectively, that hybridizes to a probe. The DNA or RNA to be analyzed can be electrophoretically separated on an agarose or polyacrylamide gel, transferred to nitrocellulose, nylon, or other suitable membrane, and hybridized with a probe using standard techniques well known in the art such as those described in sections 7.39-7.52 of Sambrook et al., (1989) Molecular Cloning, second edition, Cold Spring harbor Laboratory, Plainview, N.Y. Typically, a probe is at least about 20 nucleotides in length. For example, a probe corresponding to a 20 nucleotide sequence set forth in SEQ ID NO:3, SEQ ID NO:4, or SEQ ID NO:5 can be used to identify an identical or similar nucleic acid. In addition, probes longer or shorter than 20 nucleotides can be used. A probe can be labeled with a biotin, digoxygenin, an enzyme, or a radioisotope such as $^{32}P$.

Isolated nucleic acids provided herein also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then cart be ligated into a vector.

Antibodies

An antibody that can bind to a polypeptide having TRAIL-s activity can be made and purified using methods known to those skilled in the art (e.g., the methods described herein). For example, an antibody that can bind to a polypeptide having TRAIL-s activity can be affinity purified from the serum of an animal (e.g., a mouse, rat, rabbit, goat, donkey, horse, duck, or chicken) that received a substantially pure polypeptide having TRAIL-s activity under conditions that illicit an immune response to the polypeptide having TRAIL-s activity. In some cases, an antibody that can bind to a polypeptide having TRAIL-s activity can be purified from the supernatant of a B cell hybridoma that produces such an antibody.

An antibody that can bind to a polypeptide having TRAIL-s activity can be monoclonal or polyclonal and can be, for example, a single chain Fv, chimeric antibody, or an Fab fragment. In some cases, an antibody that can bind to a polypeptide having TRAIL-s activity can be an antibody that does not bind to other TRAIL isoforms (e.g., TRAILα, TRAILβ, and TRAILγ). An antibody that selectively binds TRAIL-s can bind an epitope contained in the sequence, TPRMKRLWAAK (SEQ ID NO:2). An antibody can be of any type, (e.g., IgG, IgM, IgD, IgA or IgY), class (e.g., IgG1, IgG4, or IgA2), or subclass. In addition, an antibody can be from any animal including birds and mammals. For example, an antibody can be a human, rabbit, sheep, or goat antibody. An antibody can be naturally occurring, recombinant, or synthetic. In addition, an antibody that can bind to a polypeptide having TRAIL-s activity can bind to a polypeptide having TRAIL-s activity at an affinity of at least $10^4$ mol$^{-1}$ (e.g., at least $10^5$, $10^6$, $10^7$, $10^8$, $10^9$, $10^{10}$, $10^{11}$, or $10^{12}$ mol$^{-1}$).

An antibody that can bind to a polypeptide having TRAIL-s activity can be prepared using any appropriate method. For example, polyclonal antibodies can be prepared using methods known in the art. See, e.g., Green et al., Production of Polyclonal Antisera, in IMMUNOCHEMICAL PROTOCOLS (Manson, ed.), pages 1 5 (Humana Press 1992) and Coligan et al., Production of Polyclonal Antisera in Rabbits, Rats, Mice and Hamsters, in CURRENT PROTOCOLS IN IMMUNOLOGY, section 2.4.1 (1992). In addition, various techniques common in the immunology arts can be used for purification and concentration of polyclonal antibodies, as well as monoclonal antibodies (Coligan, et al., Unit 9, Current Protocols in Immunology, Wiley Interscience, 1994).

Monoclonal antibodies also can be prepared using standard methods. See, e.g., Kohler & Milstein, *Nature* 256:495 (1975); Coligan et al., sections 2.5.1 2.6.7; and Harlow et al., ANTIBODIES: A LABORATORY MANUAL, page 726 (Cold Spring Harbor Pub. 1988). Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well established techniques. Such isolation techniques include affinity chromatography with Protein A Sepharose, size exclusion chromatography, and ion exchange chromatography. See, e.g., Coligan et al., sections 2.7.1 2.7.12 and sections 2.9.1 2.9.3; Barnes et al., Purification of Immunoglobulin G (IgG), in METHODS IN MOLECULAR BIOLOGY, VOL. 10, pages 79 104 (Humana Press 1992).

In addition, standard methods of in vitro and in vivo multiplication of monoclonal antibodies can be used. Multiplication in vitro can be carried out in suitable culture media such as Dulbecco's Modified Eagle Medium or RPMI 1640 medium, optionally replenished by mammalian serum such as fetal calf serum, or trace elements and growth sustaining supplements such as normal mouse peritoneal exudate cells, spleen cells, and bone marrow macrophages. Production in vitro provides relatively pure antibody preparations and allows scale up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells (e.g., osyngeneic mice) to cause growth of antibody producing tumors. Optionally, the animals can be primed with a hydrocarbon, especially oils such as pristane (tetramethylpentadecane) prior to injection. After one to three weeks, the desired monoclonal antibody can be recovered from the body fluid of the animal.

In some cases, antibodies provided herein can be made using non-human primates. General techniques for raising therapeutically useful antibodies in baboons can be found, for example, in Goldenberg et al., International Patent Publication WO 91/11465 (1991) and Losman et al., *Int. J. Cancer,* 46:310 (1990).

In some cases, antibodies provided herein can be humanized monoclonal antibodies. Humanized monoclonal antibodies can be produced by transferring mouse complementarity determining regions (CDRs) from heavy and light variable chains of the mouse immunoglobulin into a human variable domain, and then substituting human residues in the framework regions of the murine counterparts. The use of antibody components derived from humanized monoclonal antibodies can obviate potential problems associated with the immunogenicity of murine constant regions when treating humans. General techniques for cloning murine immunoglobulin variable domains are described, for example, by Orlandi et al., *Proc. Nat'l. Acad. Sci. USA,* 86:3833 (1989). Techniques for producing humanized monoclonal antibodies are described, for example, by Jones et al., *Nature,* 321:522 (1986); Riechmann et al., *Nature,* 332:323 (1988); Verhoeyen et al., *Science,* 239:1534 (1988); Carter et al., *Proc. Nat'l. Acad. Sci. USA,* 89:4285 (1992); Sandhu, *Crit. Rev. Biotech.,* 12:437 (1992); and Singer et al., *J. Immunol.,* 150:2844 (1993).

Antibodies provided herein can be derived from human antibody fragments isolated from a combinatorial immunoglobulin library. See, for example, Barbas et al., METHODS: A COMPANION TO METHODS IN ENZYMOLOGY, VOL. 2, page 119 (1991) and Winter et al., *Ann. Rev. Immunol.,* 12: 433 (1994). Cloning and expression vectors that are useful for producing a human immunoglobulin phage library can be obtained, for example, from STRATAGENE Cloning Systems (La Jolla, Calif.).

In addition, antibodies provided herein can be derived from a human monoclonal antibody. Such antibodies can be obtained from transgenic mice that have been "engineered" to produce specific human antibodies in response to antigenic challenge. Using this technique, elements of the human heavy and light chain loci can be introduced into strains of mice derived from embryonic stem cell lines that contain targeted disruptions of the endogenous heavy and light chain loci. The transgenic mice can synthesize human antibodies specific for human antigens and can be used to produce human antibody secreting, hybridomas. Methods for obtaining human antibodies from transgenic mice are described by Green et al., *Nature Genet.,* 7:13 (1994); Lonberg et al., *Nature,* 368:856 (1994); and Taylor et al., *Int. Immunol.,* 6:579 (1994).

Antibody fragments can be prepared by proteolytic hydrolysis of an intact antibody or by the expression of a nucleic acid encoding the fragment. Antibody fragments can be obtained by pepsin or papain digestion of intact antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. In some cases, an enzymatic cleavage using pepsin can be used to produce two monovalent Fab' fragments and an Fc fragment directly. These methods are described, for example, by Goldenberg (U.S. Pat. Nos. 4,036, 945 and 4,331,647). See, also, Nisonhoff et al., *Arch. Biochem. Biophys.,* 89:230 (1960); Porter, *Biochem. J.,* 73:119 (1959); Edelman et al., METHODS IN ENZYMOLOGY, VOL. 1, page 422 (Academic Press 1967); and Coligan et al. at sections 2.8.1 2.8.10 and 2.10.1 2.10.4.

Other methods of cleaving antibodies, such as separation of heavy chains to form monovalent light heavy chain fragments, further cleavage of fragments, or other enzymatic, chemical, or genetic techniques can also be used provided the fragments retain some ability to bind (e.g., selectively bind) an epitope.

The antibodies provided herein can be substantially pure. The term "substantially pure" as used herein with reference to an antibody means the antibody is substantially free of other polypeptides, lipids, carbohydrates, and nucleic acid with which it is naturally associated in nature. Thus, a substantially pure antibody is any antibody that is removed from its natural environment and is at least 60 percent pure. A substantially pure antibody can be at least about 65, 70, 75, 80, 85, 90, 95, or 99 percent pure.

Antibodies provided herein can be used in immunoassays in liquid phase or bound to a solid phase. For example, antibodies provided herein can be used in competitive and non-competitive immunoassays in either a direct or indirect format. Examples of such immunoassays include the radioimmunoassay (RIA) and the sandwich (immunometric) assay. As described herein, antibodies that can bind to a polypeptide having TRAIL-s activity also can be administered to mammals (e.g., to reduce cancer progression).

Methods

The methods and materials provided herein can be used for treating a mammal having an apoptosis-associated condition. The mammal can be any type of mammal, including, without limitation, a mouse, rat, dog, cat, horse, goat, cow, pig, monkey, or human. As used herein, the term "apoptosis-associated condition" refers to a condition, disorder, or disease in which a change in the level of apoptosis (e.g., an increase or decrease in apoptosis) in a tissue of a mammal with the condition relative to the level in a tissue of a comparable mammal without the condition causes the condition, increases the severity of the condition, or causes a symptom of the condition. Examples of apoptosis-associated conditions include, without limitation, cancer, prostate hypertrophy, HIV infection, aging, non-alcoholic fatty liver disease, and diabetes.

In some embodiments, the methods and materials provided herein can be used to decrease TRAIL-mediated apoptosis in a mammal in need thereof. For example, a mammal (e.g., a human) having a condition characterized by increased apoptosis (e.g., non-alcoholic fatty liver disease) can be administered a substantially pure polypeptide having TRAIL-s activity. In some cases, the methods and materials provided herein can be used to decrease TRAIL-mediated apoptosis in a mammal having a viral disease associated with acute lymphopenia. For example, a mammal having Avian influenza, a respiratory syncytial virus infection, a measles virus infection, or a viral hemorrhagic fever (e.g., Ebola, Hantann, and Marburg) can be administered a substantially pure polypeptide having TRAIL-s activity.

In another embodiment, the methods and materials provided herein can be used to increase TRAIL-mediated apoptosis in a mammal in need thereof. For example, a mammal (e.g., a human) having a condition characterized by decreased apoptosis (e.g., cancer) can be administered a TRAIL-s antagonist. A TRAIL-s antagonist can be any agent that inhibits binding of a polypeptide having TRAIL-s activity to its receptor, such as, for example, an antibody that specifically binds a polypeptide having TRAIL-s activity.

A substantially pure polypeptide having TRAIL-s activity or TRAIL-s antagonist can be combined with a pharmaceutically acceptable carrier prior to administration. Polypeptides having TRAIL-s activity and TRAIL-s antagonists can be administered using any suitable method (e.g., orally, intravenously, intraperitoneally, intratumorally, or subcutaneously).

A TRAIL-s antagonist or a substantially pure polypeptide having TRAIL-s activity can be administered to a mammal in any amount, at any frequency, and for any duration effective to achieve a desired outcome. For example, a TRAIL-s antagonist or a substantially pure polypeptide having TRAIL-s activity can be administered to a mammal under conditions where one or more symptoms of an apoptosis-associated condition are prevented or reduced.

In some cases, a substantially pure polypeptide having TRAIL-s activity can be administered to a mammal having a condition characterized by increased apoptosis (e.g., a viral infection) in order to reduce the level of apoptosis by 5, 10, 25, 50, 75, or more percent. For example, the level of apoptosis can be reduced such that little or no apoptosis is detected. Any appropriate method can be used to determine whether or not the level of apoptosis is reduced. For example, the level of apoptosis can be determined by performing a cell count (e.g., a viable cell count), at different time points, of one or more types of cells (e.g., lymphocytes) undergoing increased apoptosis as a consequence of an apoptosis-associated condition. The cell counts obtained at different times can be compared to determine the level of apoptosis. After administering a substantially pure polypeptide having TRAIL-s activity as described herein, the level of apoptosis can be determined again over another time interval to determine whether or not the level was reduced.

In some cases, a TRAIL-s antagonist can be administered to a mammal (e.g., a human) having a condition characterized by decreased apoptosis (e.g., cancer) in order to increase the level of apoptosis by 5, 10, 25, 50, 75, or more percent. For example, the level of apoptosis can be increased such that one or more types of cells (e.g., cancer cells) that were undergoing decreased apoptosis as a consequence of an apoptosis-associated condition are present at a reduced level or are no longer detectable. Any appropriate method can be used to determine whether or not one or more types of cells (e.g., cancer cells) are present at a reduced or undetectable level. For example, imaging techniques can be used to assess the levels of one or more types of cells (e.g., cancer cells) at various time points. In some cases, immunohistological or histopathological analyses can be performed on biological samples (e.g., blood samples and biopsy specimens) at different time points (e.g., before and after administration of a TRAIL-s antagonist) to determine whether or not the level of one or more types of cells (e.g., cancer cells) is reduced or undetectable.

In some cases, a TRAIL-s antagonist can be administered to a mammal having a condition characterized by decreased apoptosis (e.g., cancer) to reduce the progression rate of the condition (e.g., cancer) by 5, 10, 25, 50, 75, 100, or more percent. For example, the progression rate can be reduced such that no additional progression is detected. Any method can be used to determine whether or not the progression rate of a condition (e.g., cancer) is reduced. For example, the progression rate of cancer can be assessed by imaging tissue at different time points and determining the amount of cancer cells present. The amounts of cancer cells determined within tissue at different times can be compared to determine the progression rate. After administration of a TRAIL-s antagonist, the progression rate can be determined again over another time interval. In some cases, the stage of cancer after treatment can be determined and compared to the stage before treatment to determine whether or not the progression rate was reduced.

In some cases, a TRAIL-s antagonist can be administered to a mammal having cancer under conditions where progression-free survival or time to progression is increased (e.g., by 5, 10, 25, 50, 75, 100, or more percent) as compared to the median progression-free survival or time to progression, respectively, of corresponding mammals having untreated cancer. Progression-free survival and time to progression can be increased by any amount (e.g., 5%, 7.5%, 10%, 25%, 50%, 75%, 100%, or more). In addition, progression-free survival can be measured over any length of time (e.g., one month, two months, three months, four months, five months, six months or longer).

An effective amount of a TRAIL-s antagonist or a substantially pure polypeptide having TRAIL-s activity can be any amount that reduces the severity of an apoptosis-associated condition without producing significant toxicity to the mammal. If a particular mammal fails to respond to a particular amount, then the amount can be increased by, for example, two-fold. After receiving this higher dose, the mammal can be monitored for both responsiveness to the treatment and toxicity symptoms, and adjustments made accordingly. Various factors can influence the actual effective amount used for a particular application. For example, the frequency of administration, duration of treatment, and route of administration may require an increase or decrease in the actual effective amount administered.

A TRAIL-s antagonist or a substantially pure polypeptide having TRAIL-s activity can be administered once or more than once. The frequency of administration can be any frequency that reduces the severity of an apoptosis-associated condition without producing significant toxicity to the mammal. For example, the frequency of administration can be from about four times a day to about once a week, or from about once a day to about once a month, or from about once every other day to about once a year. In addition, the frequency of administration can remain constant or can be variable during the duration of treatment. As with the effective amount, various factors can influence the actual frequency of administration used for a particular application. For example, the effective amount, duration of treatment, and route of administration may require an increase or decrease in administration frequency.

An effective duration for administering a TRAIL-s antagonist or a substantially pure polypeptide having TRAIL-s activity can be any duration that reduces the severity of an apoptosis-associated condition without producing significant toxicity to the mammal. Thus, an effective duration can vary from several days to several weeks, months or years. Multiple factors can influence the actual effective duration for administering a TRAIL-s antagonist or a substantially pure polypeptide having TRAIL-s activity. For example, an effective duration can vary with the frequency of administration, effective amount, and route of administration.

A polypeptide having TRAIL-s activity provided herein also can be used to identify additional TRAIL antagonists. For example, a polypeptide having TRAIL-s activity can be labeled (e.g., with a fluorescent fluorophore or with $I^{125}$) and used in a binding assay to identify additional TRAIL antagonists, such as small molecule TRAIL antagonists. Binding assays (e.g., competitive or displacement binding assays) can be carried out using cells expressing a TRAIL receptor (e.g., TRAIL-R2), or using preparations of membranes from such cells. Large numbers of molecules, such as small molecule libraries, can be screened to identify molecules that displace binding of a labeled polypeptide having TRAIL-s activity to a TRAIL receptor. A molecule that displaces the interaction of another molecule with a receptor can interact with the receptor in the same region of the receptor. Molecules that displace binding of the labeled polypeptide having TRAIL-s activity can be evaluated for TRAIL antagonist activity using any suitable method, such as a method described herein (e.g., inhibition of skTRAIL induced cell killing). In addition, molecules that displace binding of a labeled polypeptide having TRAIL-s activity can be screened to determine whether or not they displace the binding of other labeled molecules to other receptors.

The invention will be further described in the following examples, which do not limit the scope of the invention described in the claims.

EXAMPLES

Example 1

Characterization of TRAIL-s

Cell Lines, Primary Cells, and Culture Media

Primary peripheral blood lymphocytes (PBLs) were obtained and separated by gradient centrifugation over Ficoll-Paque Plus (GE Healthcare, Piscataway, N.J.). After monocyte depletion by plastic adherence, cells were treated with 5 µg/mL of phytohemagglutinin A (PHA; Sigma, St Louis, Mo.). Non-adherent PBLs were cultured in media supplemented with IL-2 (80 U/mL) for 72 hours. Greater than 90 percent pure populations of CD4+ T cells were obtained through immunodepletion negative selection using Rosette-Sep (StemCell Technologies, Seattle, Wash.). Jurkat T cells and HEK-293T cells were obtained from the American Type Culture Collection (Manassas, Va.). Tumor cell lines 786-O, DU145, T24, WM164, WM793, and WM3211 were provided by Dr. Thomas Griffith (University of Iowa, Iowa City, Iowa). Tumor cell lines A375, Hs695t, Sk-Mel-28, WM266, and C32tg were provided by Dr. Svetomir Markovic (Mayo Clinic, Rochester, Minn.). Tumor cell lines HeLa, MCF-7, MDA-MB-468, and Ovcar5 were provided by Dr. Scott Kaufmann (Mayo Clinic, Rochester, Minn.). Cholangiocarcinomas KMC and KMCH were provided by Dr. Greg Gores (Mayo Clinic, Rochester, Minn.). Cells, as appropriate, were cultured in either RPMI 1640 or DMEM (Mediatech, Herndon, Va.) supplemented with 10% fetal calf serum (Atlanta Biologicals, Atlanta, Ga.), 100 U/mL penicillin, and 100 µg/mL streptomycin (Invitrogen, Carlsbad, Calif.). All cell lines and PBLs were cultured at 37° C. in an atmosphere containing 5% $CO_2$.

In Vitro HIV Infection of Isolated PBL

Adult human PBLs were infected with HIV IIIB (NIH AIDS Research & Reference Reagent Program, Bethesda, Md.) or mock-infected as described elsewhere (Lum, et al., *J Virol.*, 75:11128-36 (2001)).

RNA Isolation, Oligonucleotide Primers, RT-PCR and Sequencing of Products

Total RNA was isolated using TRIzol (Invitrogen). Reverse transcription (RT) and PCR amplifications were performed in a volume of 50 µL using Titanium One-Step RT-PCR kit (BD Biosciences, San Jose, Calif.) and 40 or 45 pmol of each 3'- and 5'-TRAIL-specific oligonucleotide primer (derived using GenBank accession number U37518). Forward primers, for each exon of TRAIL, included: 5'-TCTGA-CAGGATCATGGCTATG-3' (exon 1, start codon underlined; SEQ ID NO:6); 5'-CAGCCTGGGACAGACCT-3' (internal exon 1 sequence; SEQ ID NO:7), 5'-CAGGACAAGTACTC-CAAAAGT-3' (exon 2; SEQ ID NO:8); 5'-TGAGAAC-CTCTGAGGAAACC-3' (exon 3; SEQ ID NO:9); and 5'-AG-CAACAAAATATTTCTCCCCTA-3' (exon 4; SEQ ID NO:10). Reverse primers included: 5'-ACTAAAAAGGC-CCCGAAAA-3' (exon 5; SEQ ID NO:11); 5'-CCTCTG-GTCCCAGTTATGT-3' (exon 4; SEQ ID NO:12); 5'-TG-GTTTCCTCAGAGGTTCTC-3' (exon 3; SEQ ID NO:13); and 5'-ACGGAGTTGCCACTTGACTT-3' (exon 2; SEQ ID NO:14). β-actin specific oligonucleotides (forward primer, 5'-GAAACTACCTTCAACTCCATC-3' (SEQ ID NO:15) and reverse primer, 5'-CGAGGCCAGGATGGAGCCGCC-3' (SEQ ID NO:16)) were used as amplification controls (GenBank accession number NM_001101). Conditions for RT-PCR were as follows: a reverse transcription step at 50° C. for 60 minutes followed by an initial denaturation step at 94° C. for 2 minutes, followed by 30 cycles (TRAIL) or 25 cycles (Actin) of denaturation for 30 seconds, annealing for 1 minute at 55° C., extension at 72° C. for 45 seconds and a final extension step at 72° C. for 5 minutes. PCR products were electrophoresed on 2% or 3% agarose gels containing ethidium bromide and visualized under UV transillumination.

Bands of interest were excised from agarose gels and isolated using the QIAquick gel extraction kit (Qiagen, Valencia, Calif.). Products were ligated into the pGEM-T easy cloning vector (Promega, Madison, Wis.) and transformed into *E. coli*. Isolated colonies containing the plasmid were cultured and plasmid DNA was recovered using the Perfectprep Plasmid Isolation Kit (Eppendorf North America, Westbury, N.Y.). Plasmids were sequenced using T7 or SP6 site-specific primers on an ABT Prism 377 DNA sequencer (Applied Biosystems, Foster City, Calif.).

Expression Vectors and Transfection of Cultured Cells

The complete cDNA coding sequence of TRAIL-s was amplified by RT-PCR as described herein, using the BamHI site-containing forward primer 5'-C GGATCCATGGCTATGATGG-3' (SEQ ID NO:17; restriction site underlined just upstream of TRAIL start codon) and reverse primer spanning the exon 2-5 splice junction 5'-TTATTTTGCGGCCCAGAGCCTTTTCAT-TCTTGGAGTCTTTC-3' (SEQ ID NO:18). The PCR product was cloned into the pGEM-T-easy vector as described herein, digested with BamHI and EcoRI, and then directionally subcloned into expression vectors (i.e., pGEX-KG, HA-pcDNA3, pEGFPC1, and pEGFPN1 (Clontech, Mountain View, Calif.)) using standard protocols to produce GST-, HA-, and GFP-tagged constructs of TRAIL-s, respectively.

HEK-293T cells were transfected using Lipofectamine 2000 reagent (Invitrogen). Twenty-four hours after transfection, culture supernatants and cell pellets were collected for experiments and expression analysis. Transfection of primary CD4+ T cells was performed using the Nucleofactor transfection system and reagents (T-23 program; Amaxa, Gaithersburg, Md.). Transfection efficiency was monitored by fluorescence (e.g., for GFP and GFP-TRAIL-s expression) or by Western blot analysis (e.g., for HA and HA-TRAIL-s) as described herein.

Recombinant GST-tagged TRAIL-s was produced in *E. coli* DH5α, transformed with pGEX vector containing TRAIL-s, and cultured in 1 L of LB medium containing 50 µg/mL of Ampicillin to an A600 of 0.6 to 0.8. Synthesis of GST-TRAIL-s was induced by addition of 0.1 mM IPTG for 3 hours at 37° C. Bacteria were collected by centrifugation, washed with PBS, and resuspended in 10 mL of STE buffer (10 mM Tris-HCl, 1 mM EDTA, 150 mM NaCl) supplemented with protease inhibitors. Freshly prepared lysozyme solution was added to a final concentration of 100 µg/mL, and then incubated on ice for 15 minutes. Just before sonication for a total time of 1 minute, 10 mM DTT and 1.4% Sarkosyl were added and the suspension was mixed thoroughly. Cell debris was removed by pelleting. The supernatant was supplemented with 4% Triton X-100 and additional STE Buffer to 20 mL, and was incubated at room temperature for 30 minutes. The lysate was purified over a glutathione agarose column, and GST-TRAIL-s bound to the column was eluted with glutathione buffer (10 mM Tris-HCl, 1 mM DTT, and 10 mM Glutathione). Protein concentrations of purified GST (control) or GST-TRAIL-s were determined using a Bradford absorbance colorimetric assay (Bio-Rad, Hercules, Calif.).

Antibodies

Fluorescently tagged anti-TRAIL antibody (clone RIK-2) as well as Annexin V-PE, Annexin V-FITC, and propidium iodide were obtained from BD Biosciences (San Jose, Calif.). Antibodies against the HIV antigen p24 were obtained from Immunodiagnostics (Woburn, Mass.). Mouse monoclonal antibodies (MAbs) to TRAIL-R1 (clone M271), TRAIL-R2 (clone M412), TRAIL-R3 (clone M430), and TRAIL-R4 (clone 445) were obtained from Dr. David Lynch (Immunex Corporation; Amgen, Thousand Oaks, Calif.). Phycoerythrin (PE)-conjugated anti-TRAIL-R2 antibodies, as well as secondary anti-mouse PE antibodies for flow cytometry were obtained from R & D Systems (Minneapolis, Minn.). Anti-GST antibodies for flow cytometry were obtained from Martek Biosciences (Columbia, Md.). Western blotting control antibodies for PCNA (clone PC10) and actin (clone C2), HRP-conjugated secondary antibodies against mouse and rabbit immunoglobulins, and Protein A/G-Plus beads were purchased from Santa Cruz Biotechnology (San Jose, Calif.). HRP-conjugated Protein-A for use in Western blotting was purchased from GE Healthcare (Piscataway, N.J.). Anti-hemagglutinin (anti-HA) antibody was purchased from Boehringer-Mannheim (Indianapolis, Ind.).

Protein Detection by Western Blot Analysis

Cells were lysed using 150 mM NaCl, 0.1% Triton X-100, 10 mM Tris-HCl, pH 7.6, and mini-cØmplete protease inhibitor tablets (Roche Applied Science, Indianapolis, Ind.). Following centrifugation at 14,000 g for 15 minutes, protein samples were analyzed for protein concentration, and equivalent amounts of the protein samples were electrophoresed on 15% SDS-polyacrylamide gels and transferred to Immobilon-P membranes (Millipore, Billerica, Mass.). Membranes were blocked in Tris-buffered saline containing 0.2% Tween-20 and 2% BSA, and blotted in a 1:1000 dilution of primary antibody (e.g., H-257, K-18 (Santa Cruz Biotechnology, San Jose, Calif.), and anti-HA (Boehringer-Mannheim, Indianapolis, Ind.)) followed by a 1:10,000 dilution of an appropriate HRP-conjugated secondary antibody (e.g., anti-mouse HRP, anti-goat HRP, or anti-rabbit HRP). Membranes were developed using ECL Western blotting detection reagents (GE Healthcare). Equal protein loading was confirmed by re-blotting membranes for Proliferating Cell Nuclear Antigen (PCNA) using a mouse anti-PCNA-specific antibody (PC10; Santa Cruz Biotechnology), or by re-blotting membranes for actin using an anti-actin antibody (clone C2; Santa Cruz Biotechnology).

Induction of Apoptosis and Assessment

Cell death was induced through the addition of Fas-agonist CH-11 antibody (Upstate Biotechnology, Lake Placid, N.Y.) at 100 ng/mL, the addition of recombinant Superkiller TRAIL (skTRAIL; Axxora, San Diego, Calif.) at 15 ng/mL, or the addition of leucine zipper TRAIL (LZ TRAIL) at 25 ng/mL (Dr. David Lynch, Immunex) to culture media. Where indicated, cells were pretreated with antagonistic TRAIL antibody clone 2E5 (Axxora) or isotype control antibody at a concentration of 5 µg/mL to determine whether TRAIL receptor/TRAIL complexes were functional. Cell death was quantitated using Trypan blue staining, flow cytometry for Annexin V and/or propidium iodide staining (BD Biosciences), caspase-3 fluorogenic activity assays, and CellTiter-Glo ATP and luciferase-based viability detection means. Viability also was assessed using MTS reduction assays (Promega, Madison, Wis.). Viability was calculated by subtracting the percentage of dead cells from the total number of cells counted/assessed by the indicated method. PBL effector killing of the TRAIL-sensitive target Jurkat T cells was examined in co-culture experiments. The target Jurkat T cells were pre-stained with DiO (3,3'-dioctadecyl oxacarbocyanine perchlorate; Molecular Probes, Eugene, Oreg.) to identify them in co-culture with PBLs by incubating them at $1 \times 10^6$ cells per mL in 500 nM DiO in PBS for 5 minutes at room temperature in the dark, followed by washing with PBS. PBLs were washed with PBS before use, and then combined in fresh complete medium with the labeled Jurkat cells at the indicated ratios of effectors:targets. Where indicated, neutralizing anti-TRAIL antibody (clone 2E5) was also added to the cell mixture. After 6 hours, cells were resuspended in Annexin binding buffer, stained with Annexin V-Cy5 (BD Biosciences, San Jose, Calif.) before analysis on a FACSCalibur instrument (BD Biosciences). Data are expressed as the insult-specific (e.g., TRAIL- or Fas-specific) apoptosis, and calculated as the percent apoptosis following insult minus the percent apoptosis in control samples. Relative inhibition of apoptosis was calculated as the insult-specific percent apoptosis minus the reduced apoptosis percentage, divided by the insult-specific apoptosis.

Monitoring of TRAIL and TRAIL Receptors at the Cell Surface

Flow cytometry was used to determine surface expression of TRAIL receptors, as described elsewhere (Lum, et al., *J. Virol.*, 75:11128-36 (2001)). Briefly, $10^6$ cells in minimal volume were incubated with 1 µg/mL of primary antibodies (e.g., anti-TRAIL-R1 (clone M271), anti-TRAIL-R2 (clone M412), anti-TRAIL-R3 (clone M430), or anti-TRAIL-R4 (clone 445); Immunex Corporation) in PBS containing 1% BSA for 1 hour on ice, before labeling with phycoerythrin (PE)-conjugated anti-mouse secondary antibodies. Flow cytometry was performed on a FACSCalibur bench top cytometer and Macintosh workstation running CellQuest software (BD Biosciences), and a minimum of 20,000 events were counted for each sample.

Briefly, $10^6$ cells in 100 µL volume were incubated with 5 µg/mL of primary antibodies in PBS containing 1% BSA for 1 hour on ice, then stained with PE-conjugated anti-mouse secondary antibodies. TRAIL expression was assessed by flow cytometry using the directly conjugated antibody RIK-2 (BD Pharmingen). Annexin V staining was performed by washing treated or control cells with PBS before suspension in binding buffer (10 mM HEPES/NaOH, pH 7.4, 140 mM NaCl, 2.5 mM $CaCl_2$). Next, 10 µg Annexin V-FITC or Annexin-PE was added to appropriate samples, and incubated at room temperature for 15 minutes before flow cytometry. Where indicated in the text, flow samples were also gated on parameters of GFP-positivity, or alternately by light scatter characteristics. Flow cytometry was performed on a FACSCalibur benchtop cytometer and Macintosh workstation running CellQuest software (BD Biosciences), and a minimum of 20,000 events were counted for each sample. Concentrations of TRAIL in cell culture supernatants were determined by commercial ELISA (Cell Sciences, Canton, Mass.) according to manufacturer's protocol.

TRAIL-s Depletion Experiments

Immunodepletion of TRAIL-s from the supernatants of transfected HEK-293T, mock-infected PBL, or HIV-infected PBL cells was performed by adding anti-TRAIL-s rabbit antisera (or preimmune sera from the same rabbit as control) and Protein-A/G sepharose beads to cell supernatants followed by rocking at 4° C. for two hours. Beads were pelleted by centrifugation, and removal of the TRAIL-s from transfected HEK-293T supernatants or HIV-infected supernatants was confirmed by Western blot following depletion. PBS, supernatants from mock-infected PBLs, or supernatants from HIV-infected PBLs were then used to pre-treat TRAIL-sensitive Jurkat target cells for 30 minutes before killing with skTRAIL at 10 or 15 ng/mL. Supernatants were generated by suspending $1 \times 10^7$ washed PBLs per 100 µL in PBS for 60 minutes at 37° C. The supernatants were divided into portions that were or were not immunodepleted.

TRAIL-s RNA Interference (RNAi) Experiments

RNA interference (RNAi) of TRAIL-s was achieved through transfection of shRNA oligonucleotides (Dharmacon, Lafayette, Colo.) targeting the TRAIL-s mRNA. Controls included untransfected cells, empty vector transfection, transfection with non-RISC interacting shRNA oligonucleotides, transfection with shRNA oligonucleotides specific for of Lamin A/C mRNA, and transfection with non-targeting shRNA oligonucleotides tagged with Cy-3 (to determine transfection efficiency). Cells were plated 24 hours before transfection in either 24 or 96 well plates, at concentrations of 30,000 cells/well and 3,000 cells/well, respectively, in antibiotic-free media. Optimal concentrations for Lipofectamine 2000 and the shRNA oligonucleotides were determined empirically to be 1 µL and 0.2 µL Lipofectamine 2000 per well in 24-well and 96-well plates, respectively, and shRNA oligonucleotides were used at 30 mM. RNA interference was confirmed by Western blot 48 hours after transfection. To assess functional consequences of TRAIL-s RNA interference, killing curves were created for the transfected cells by treating across a range of skTRAIL concentrations. Cell death was assessed by MTS reduction assay, by flow cytometry for light scatter, and by Annexin V binding 16 hours after skTRAIL was added.

Statistical Analysis

Where indicated, statistical analysis was performed comparing treatment groups against appropriate control groups using a student's t-test. P-values less than 0.05 were considered significant.

Antibody Production and Screening

Polyclonal antisera against the neoepitope C-terminus of TRAIL-s was raised in rabbits immunized with recombinant dodecapeptide, CTPRMKRLWAAK (SEQ ID NO:19), conjugated to keyhole limpet hemocyanin (KLH).

The unique carboxyl terminal 11 amino acids encoded by TRAIL-s (SEQ ID NO:19) were synthesized and conjugated to KLH through a Cysteine residue also added to the N-terminus of the peptide sequence using an Apex 396 Peptide Synthesizer. The purified peptide was used in the immunization of rabbits for the generation of polyclonal antisera. After both the initial immunization as well as two subsequent boosts of antigen, the rabbits were bled and the raw sera used to assess their reactivity to TRAIL-s produced by HA tagged TRAIL-s overexpressing cells. Reactivity of each test bleed was compared with pre-immunization sera taken from the same rabbits. After a robust response developed, terminal bleeds were taken. For generation of monoclonal antibodies, Balb/c mice were immunized with KLH-conjugated TRAIL-s C-terminal peptide. Splenic fusions were generated, and hybridomas were assessed for production of reactive antibodies through ELISA and Western blotting techniques. Single-cell clones expressing anti-TRAIL-s antibodies were expanded into tissue culture flasks and conditioned media collected after 1 week of growth. Immunoglobulin was purified by passage of the conditioned media over a protein-A column, washed, and eluted with ImmunoPure IgG Elution Buffer. The eluate was neutralized with 1 M Tris, pH 9.2 and dialyzed against PBS before sterile filtration and stored in aliquots at −80° C.

TRAIL-R2 Staining Interference and Knockdown Experiments $10^6$ Jurkat or HeLa cells were incubated on ice with 200 ng of GST, GST-TRAIL-s fusion protein, or 100 ng of skTRAIL for 30 minutes before washing once with PBS and staining for surface expression of TRAIL-R2 (as described herein). For experiments addressing TRAIL-s binding of TRAIL-R2 through knockdown, a 21-bp sequence that has been used to silence endogenous DR5 (5'-AAGACCCTTGTGCTCGT-TGTC-3' (SEQ ID NO:20)) was inserted into a plasmid, pCMS-4.eGFP.HIP, that contains an H1 promoter for shRNA expression, a CMV promoter for expression of shRNA-resistant cDNAs, and an SV-40 promoter controlling EGFP expression. For reconstitution with shRNA-resistant DR5, cDNA encoding full-length DR5 was amplified from Jurkat cell RNA, cloned into the pCMS-4.eGFP.H1P plasmid using Eco RV and Not I restriction enzymes, and mutated at the shRNA target sequence to 5'-AAAACACTAGTTCTAG-TAGTC-3' (SEQ ID NO:21) by site-directed mutagenesis. Integrity of the inserts was confirmed by sequencing. The plasmid was then transfected into Jurkat T cell leukemia cells by electroporation at 300 V for 10 milliseconds using a BTX 820 square wave electroporator. After 24 hours, cells were assayed for their ability to bind GST-TRAIL-s.

HIV-Infected T Cells are TRAIL Sensitive and Express TRAIL, but do not Undergo Paracrine TRAIL-Induced Death.

PBLs infected with HIV increased the expression of TRAIL-R1, -R2, and -R4 four days after infection as determined by flow cytometry (FIG. 1A), and by RT-PCR. PBLs from HIV-infected patients exhibited an enhanced susceptibility to TRAIL-mediated cell death, as has been demonstrated elsewhere (Lum et al., *J. Virol.*, 75:11128-36 (2001)). TRAIL expression was increased in both HIV-infected and mock-infected cells from the same cultures (FIGS. 1B and 1E). Co-staining for the HIV antigen p24 revealed that the increase in TRAIL expression occurred within the population of PBLs also staining positive for p24 (FIG. 1E). Soluble TRAIL production was increased by HIV-infected PBLs (FIG. 1C). Antagonistic TRAIL antibody clone 2E5 activity was confirmed in Jurkat T cells treated with recombinant TRAIL. Mock-infected or HIV-infected PBL cultures were treated with antagonistic TRAIL antibody clone 2E5 or isotype control antibody and assessed for cell viability (FIG. 1D). Cell viability of HIV-infected cultures was not changed as a result of the addition of antagonistic anti-TRAIL antibody, indicating that the function of either TRAIL, TRAIL receptor(s), or the interaction of TRAIL with TRAIL receptor(s) was antagonized in HIV-infected cultures.

HIV Infected PBLs Produce a Soluble Inhibitor of TRAIL-Mediated Cell Death.

Figure 2:
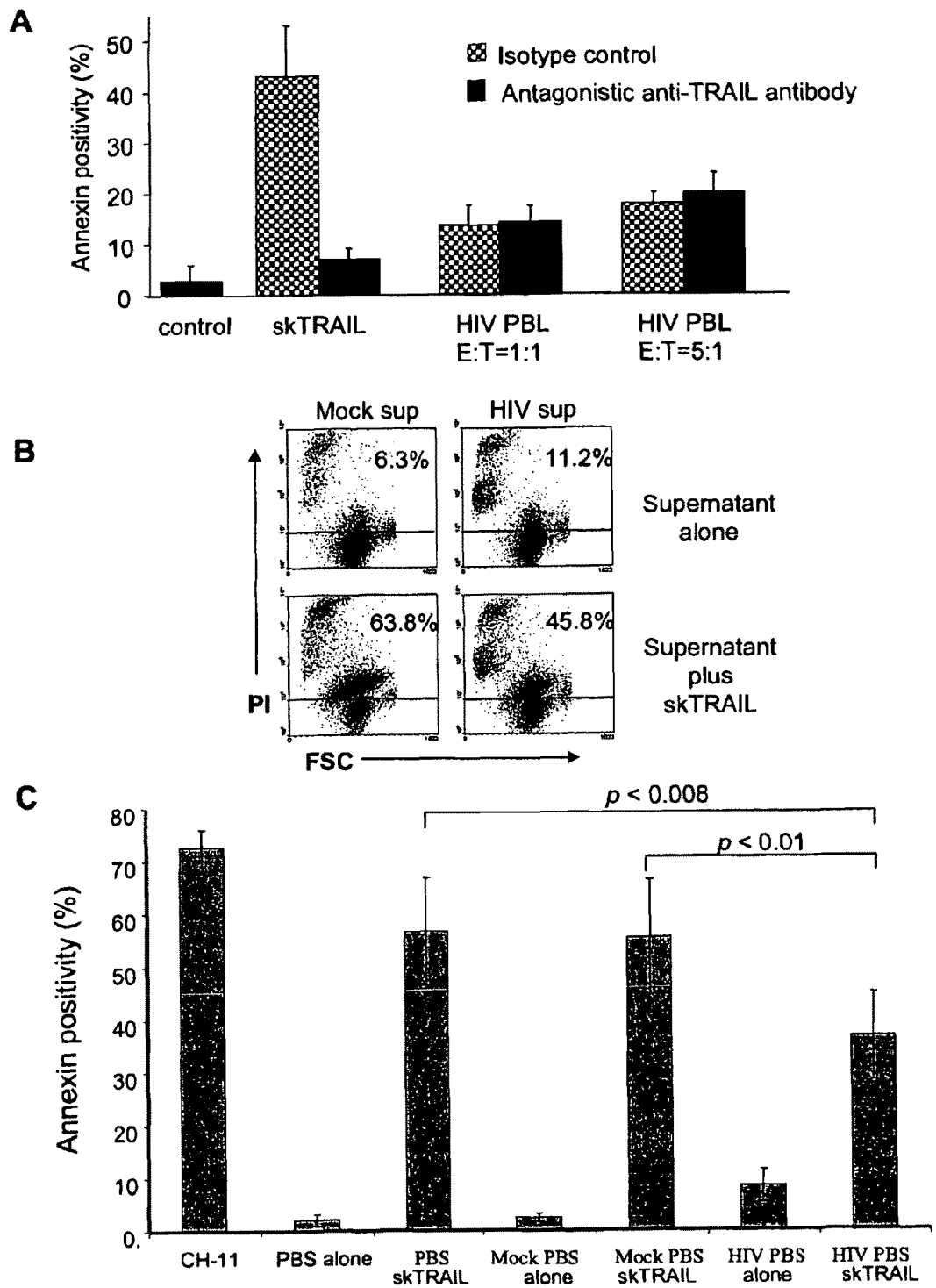
FIG. 2. (A) Effect of anti-TRAIL antibody on the viability of HIV infected Jurkat T cells. DiO-labeled Jurkat T cells were co-incubated with recombinant skTRAIL or with mock- or HIV-infected PBLs at the indicated effector-to-target ratios in the presence or absence of isotype control antibody or neutralizing anti-TRAIL antibody. Apoptosis was assessed in the Jurkat cells by gating on the DiO positive cells and measuring Annexin V-PE positivity. Data from three experiments (error bars represent the standard deviation). (B) Blockade of recombinant TRAIL induced death by preincubation in supernatant from HIV infected PBLs. HIV-infected or mock-infected PBLs were incubated at high density for 1 hour at 37° C. in PBS, the cells were removed, and the resulting PBS supernatants were used to treat Jurkat cells. Jurkat T cells treated with PBS supernatant alone were analyzed for cell death by propidium iodide (PI) permeability (top panels). Jurkat T cells also were preincubated for 1 hour with PBS supernatant from mock- or HIV-infected PBLs, treated with skTRAIL, and analyzed for PI permeability (bottom panels). Results are representative of three independent experiments. (C) Supernatants from HIV infected cells reduce TRAIL induced apoptosis. Jurkat T cells were incubated with PBS alone, or with PBS supernatant from mock- or HIV-infected PBLs. The cells were then treated with skTRAIL and analyzed for apoptosis by Annexin V staining. The Fas-agonist antibody CH-11 was included as a positive control, and the graph presents the means from six experiments, ±s.e.m.

A cytotoxicity assay was performed using TRAIL-sensitive Jurkat T cells as targets and HIV-infected PBLs as effector cells. Superkiller TRAIL (skTRAIL) induced significant Jurkat T cell death, which was inhibited by anti-TRAIL antibody. The minimal levels of Jurkat T cell death induced by HIV-infected PBLs were not affected by anti-TRAIL antibody, indicating that TRAIL produced by HIV-infected cells is non-functional or antagonized (FIG. 2A).

HIV- or mock-infected PBLs were incubated at high concentration in PBS for 90 minutes, the cells were pelletal, and the resulting supernatant was tested for the ability to induce death or inhibit TRAIL-induced death. Incubation of Jurkat T cells with supernatant from mock-infected PBLs resulted in minimal death. Incubation of Jurkat T cells with HIV-infected PBL cell supernatant caused a slight increase in the number of PI positive cells (11.2%), while treatment of Jurkat T cells with skTRAIL resulted in significant death. Preincubation of Jurkat T cells with mock-infected PBL cell supernatant did not impact skTRAIL-induced death. However, preincubation of Jurkat T cells with HIV-infected PBL cell supernatant reduced the amount of skTRAIL-induced death from 63.8% to 45.8% (FIG. 2B). The inhibitory effect of HIV-infected PBL cell supernatant was TRAIL specific, as HIV-infected PBL cell supernatant significantly inhibited skTRAIL-induced death of Jurkat T cells (p<0.008) but had no impact on apoptosis induced by the agonistic anti-Fas clone CH11 (FIG. 2C).

HIV-Infected Cells Express a Novel TRAIL Splice Variant.

Figure 3:
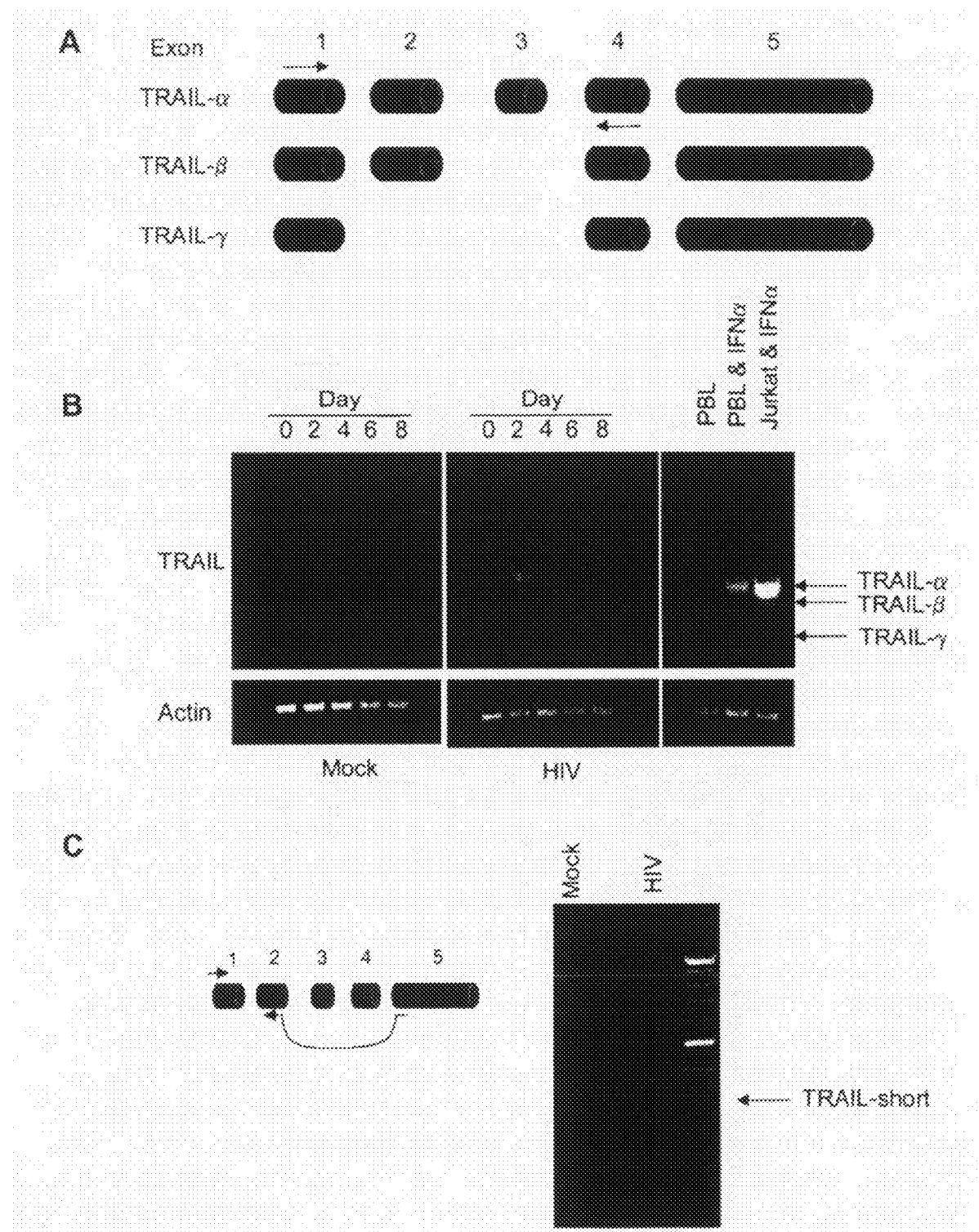
FIG. 3. (A) Schematic of the genomic organization of TRAIL indicating the transcripts which encode TRAILα, β, and γ. Arrows indicate the position of primers designed to identify TRAILα, β, and γ transcripts. (B) TRAIL isoform expression in PBLs infected with HIV. HIV- or mock-infected PBLs, cultured in IL-2, were analyzed at the indicated time points for TRAIL message using primers that amplify TRAIL-α, β, and γ. As controls, untreated PBLs, PBLs treated with interferon-α, or Jurkat T cells treated with interferon-α were used to identify TRAIL-α, β, and γ. RT-PCR for actin served as a control. (C) Novel TRAIL splice variant expression in HIV-infected cells, termed TRAIL-short (TRAIL-s). Arrows indicate position of primers designed to identify TRAIL-s.

Three soluble pro-apoptotic splice variants of TRAIL have previously been described: TRAILα, encoded by all 5 exons; TRAILβ in which exon 3 is excised; and TRAILγ in which both exons 2 and 3 are excised (FIG. 3A). Primers that are known to amplify all three variants were used to perform RT-PCR on HIV-infected or mock-infected PBL. On day 0, no TRAIL message was detectable in mock- or in HIV-infected PBLs. Mock-infected PBLs that were cultured in IL-2 exhibited increased expression of TRAILα after day 2 post-infection. In HIV-infected PBL, TRAILα, TRAILβ and TRAILγ were detectable day 2 post-infection (FIG. 3B).

A novel TRAIL RT-PCR product was amplified from HIV-infected PBLs but not mock-infected PBLs using a sense primer from exon 1 (SEQ ID NO:6) and an antisense primer from exon 5 (SEQ ID NO:11). The size and sequence of the amplified product suggested excision of exons 3 and 4. A sense primer from exon 1 (SEQ ID NO:6) and an antisense primer spanning exons 2 and 5 (SEQ ID NO:18) amplified a product in HIV-infected cells, but not mock-infected cells (FIG. 3C) that was confirmed by sequencing to be a splice variant (GenBank® GI Number 112820323). This splice variant was termed TRAIL short (TRAIL-s). The nucleotide sequence of TRAIL-s includes a frame shift, resulting in a premature stop codon within exon 5, and a novel carboxyl terminal amino acid sequence, TPRMKRLWAAK (SEQ ID NO:2).

TRAIL-s Binds Death-Inducing TRAIL Receptors and Inhibits TRAIL-Induced Apoptosis.

Figure 4:
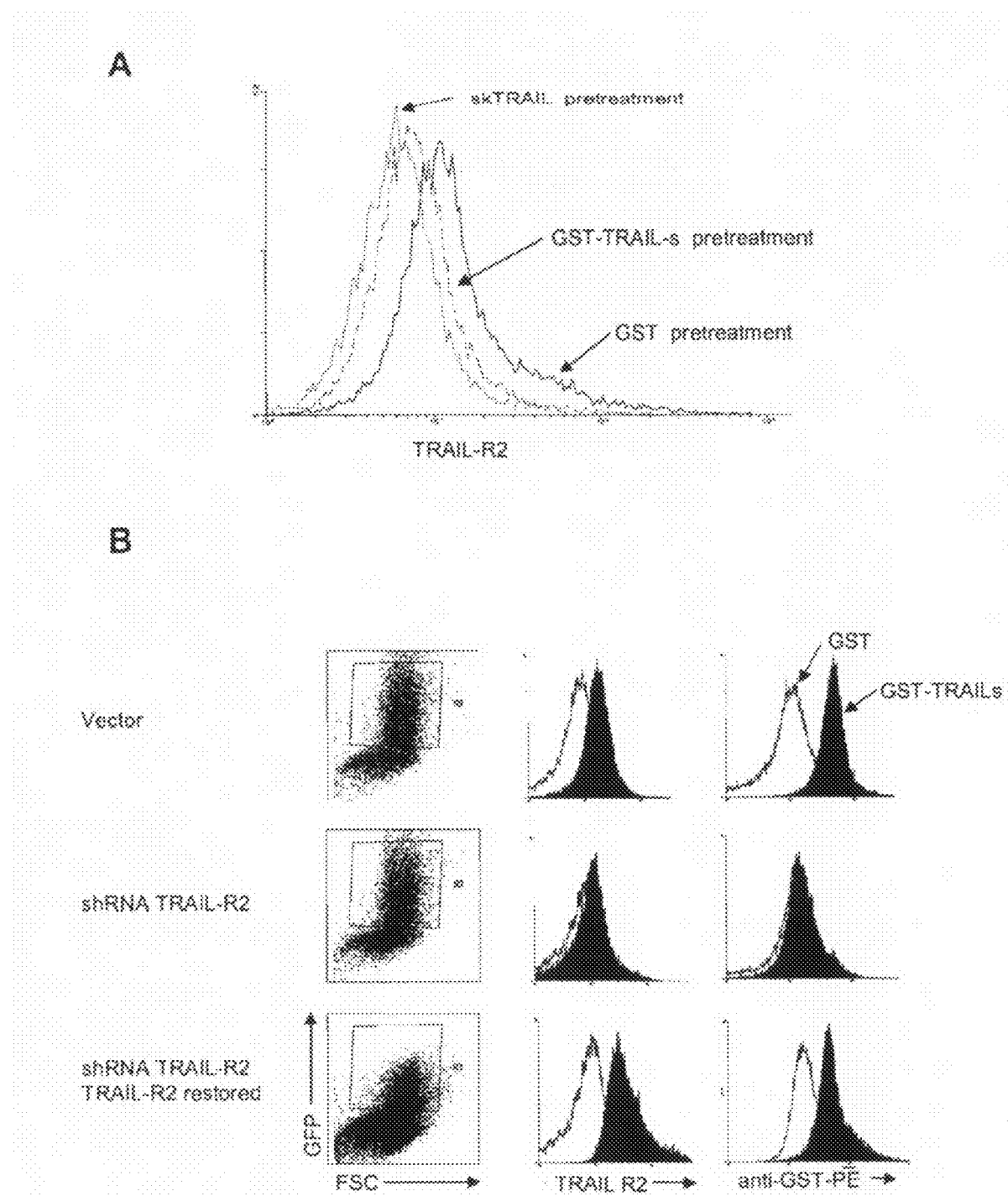
FIG. 4. (A) Flow cytometry detection of TRAIL-R2 in the presence of TRAIL-s. Jurkat T cells were stained for surface TRAIL-R2 expression following pretreatment with skTRAIL, GST, or GST-TRAIL-s recombinant protein. Pretreatment of cells with GST alone resulted in identical staining for TRAIL-R2 as untreated cells. (B) Effect of TRAIL-R2 expression on TRAIL-s interaction with cells. Jurkat T cells were transfected with constructs expressing GFP alone, GFP and shRNA for TRAIL-R2 knockdown, or GFP and shRNA for TRAIL-R2, plus an additional TRAIL-R2 re-expression sequence modified to be resistant to the encoded shRNA. GFP positive cells were specifically analyzed for TRAIL-R2 expression, and for binding of GST alone or GST-TRAIL-s. Cells transfected with shRNA for TRAIL-R2 demonstrated loss of GST-TRAIL-s binding (middle row), but this binding was restored upon re-expression of TRAIL-R2 (bottom row).

Jurkat T cells or HeLa cells, both of which express TRAIL-R1 and -R2, were analyzed following treatment with skTRAIL to determine if occupying TRAIL receptors with skTRAIL blocked the ability to detect TRAIL-R1 and/or TRAIL-R2 with receptor-specific antibodies. skTRAIL pretreatment prevented receptor detection in each cell type (FIG. 4A and data not shown). Pretreatment of Jurkat T cells (FIG. 4A) or HeLa cells (data not shown) with GST-TRAIL-s also prevented detection of TRAIL-R2 by antibody (FIG. 4A), but did not alter detection of TRAIL-R1, indicating that GST-TRAIL-s binds to TRAIL-R2. To confirm binding of TRAIL-s to TRAIL-R2, Jurkat T cells were transfected with: 1) GFP and shRNA for TRAIL-R2; or 2) GFP, shRNA for TRAIL-R2, and a coding sequence for TRAIL-R2, which was not inhibited by shRNA. GFP-expressing cells were monitored for TRAIL-R2 expression monitored and binding of GST TRAIL-s (FIG. 4B). Vector control cells had detectable TRAIL-R2 and GST-TRAIL-s bound significantly. In contrast, TRAIL-R2 expression and GST-TRAIL-s binding were both inhibited by the TRAIL-R2 shRNA. Cells in which TRAIL-R2 expression was restored, exhibited restored detection of TRAIL-R2 and binding of GST-TRAIL-s. In cells where TRAIL-R2 expression was inhibited, GST-TRAIL-s binding was minimal, suggesting that TRAIL-s does not bind significantly to other TRAIL receptors which are present on Jurkat T Cells.

TRAIL-s is the TRAIL Inhibitor Produced by HIV-Infected Cells.

Figure 5:
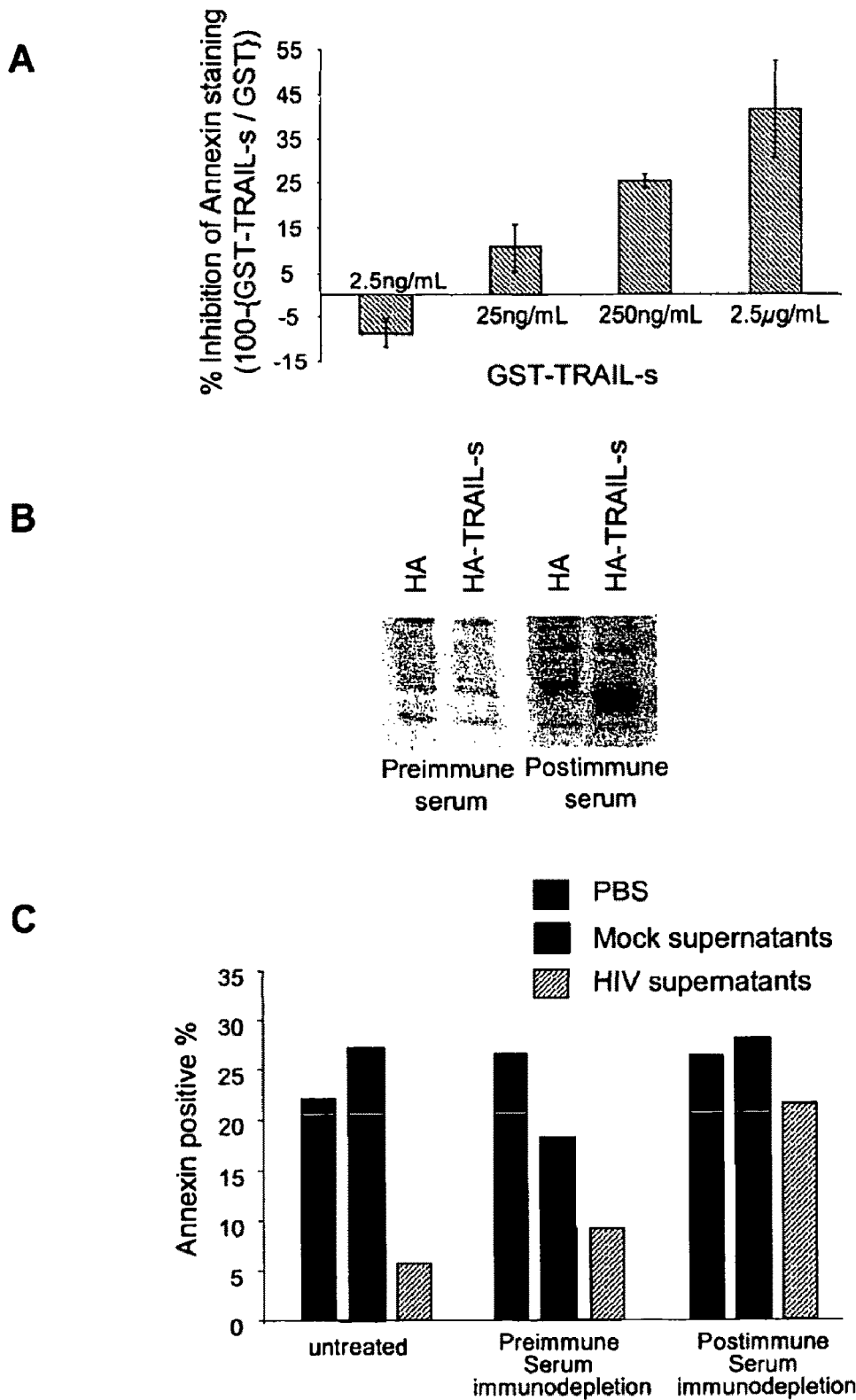
FIG. 5. (A) TRAIL-induced apoptosis is reduced in Jurkat T cells pretreated with recombinant GST TRAIL-s. Recombinant GST-TRAIL-s was used to pre-treat Jurkat T cells at the indicated doses, followed by treatment of cells with skTRAIL. Cell death was analyzed by Annexin V staining, and inhibition of Annexin staining was calculated relative to control. Means of three experiments are presented and error bars represent the standard deviations. (B) TRAIL-s specific polyclonal antibody detection of TRAIL-s. A polyclonal antiserum was raised against the novel carboxyl terminus of TRAIL-s and tested by Western blotting. (C and D) TRAIL-s immunodepleted supernatants from HIV-infected PBLs do not protect Jurkat T cells from recombinant TRAIL-medicated death. PBS, PBS supernatants from mock-infected PBLs, or PBS supernatants from HIV-infected PBLs were left untreated or immunodepleted with either the pre-immune or post-immune anti-TRAIL-s antisera. Jurkat T cells were pretreated with the supernatants, then treated with skTRAIL, and analyzed by Annexin V for apoptosis.
Figure 5:
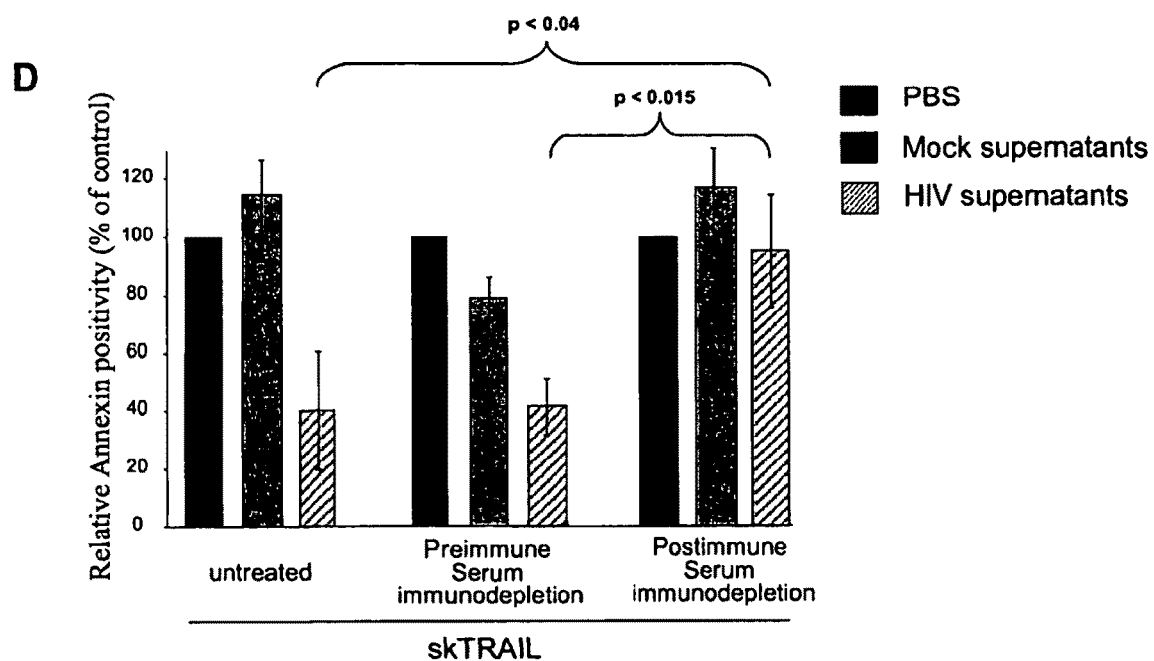

Jurkat cells were treated with GST-TRAIL-s or GST control and stimulated with recombinant TRAIL. Pretreatment of TRAIL-sensitive cells with GST-TRAIL-s produced a dose-dependent inhibition of TRAIL-induced death. At doses of 250 ng/mL, 22% of TRAIL-specific apoptosis was inhibited, increasing to 40% inhibition of TRAIL-specific apoptosis with 2.5 µg/mL of recombinant GST-TRAIL-s. These results confirm that TRAIL-s is a TRAIL antagonist (FIG. 5A). A polyclonal antibody targeted to the unique carboxyl-terminal amino acid sequence of TRAIL-s (FIG. 5B) was used to immunodeplete supernatants from HIV-infected cells. The TRAIL-s supernatants were tested to determine whether the immunodepletion altered the ability of these supernatants to inhibit TRAIL-induced death (FIG. 5C). Untreated supernatant from HIV-infected cells inhibited skTRAIL-induced cell death of Jurkat T cells. Supernatants from HIV-infected cells immunodepleted with pre-immune serum also inhibited skTRAIL-induced Jurkat T cell death. However, supernatants that were immunodepleted using post-immune serum raised against TRAIL-s did not inhibit skTRAIL-induced Jurkat T cell death, demonstrating that TRAIL-s is the factor contained within supernatants from HIV-infected cells that causes resistance to TRAIL-mediated cell death. Similar results were obtained in another experiment (FIG. 5D).

TRAIL-s is Expressed by HIV-Infected Cells In Vivo.

Figure 10:
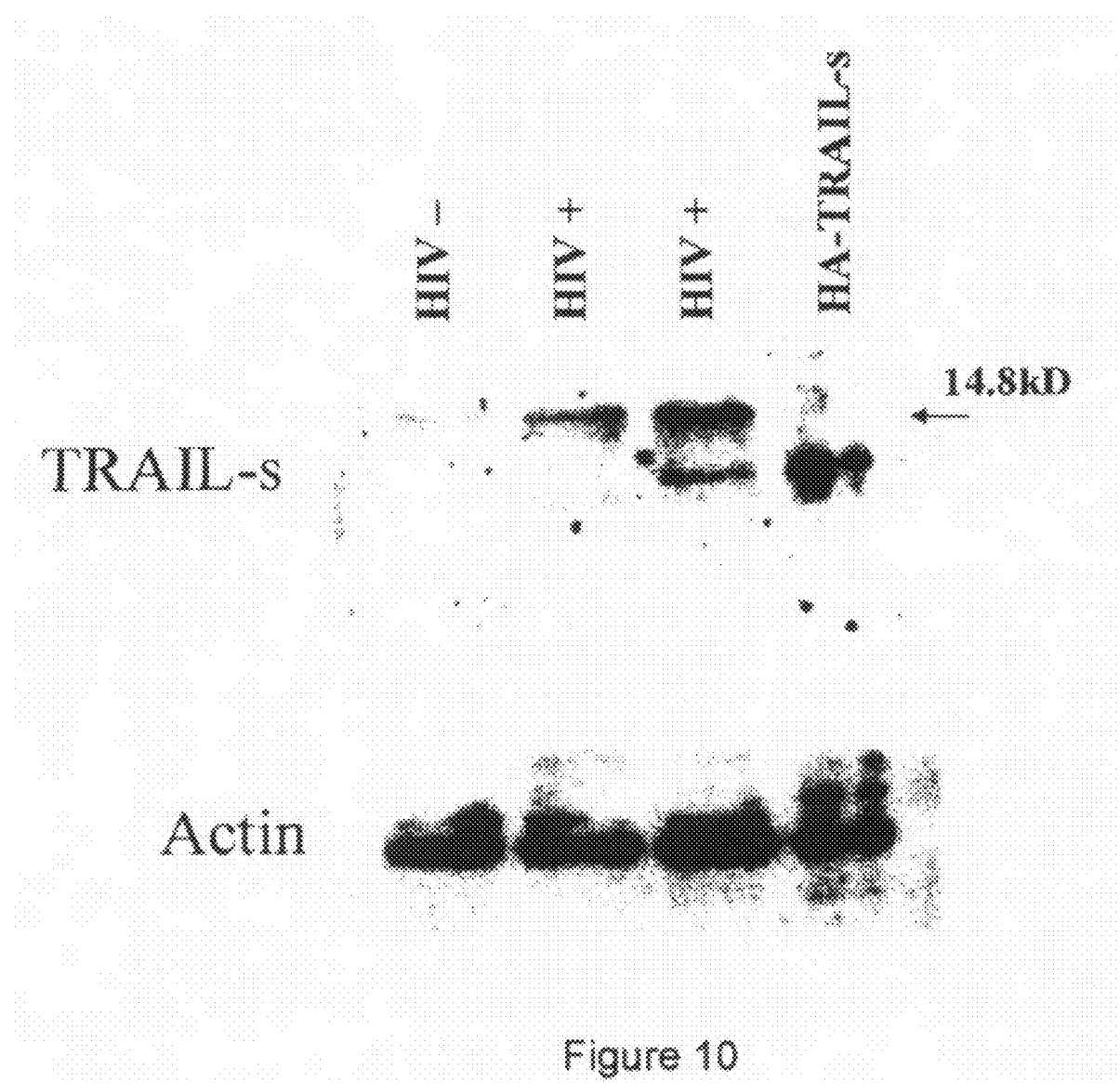
FIG. 10. TRAIL-s expression in CD4+ T cells from HIV-infected patients.

Plasma from HIV-infected patients with a wide range of viral replication was assessed by Western blot. Cell lysates from HIV-infected patients and plasma from HIV-infected patients with a wide range of viral replication was assessed by western blot. FIG. 10 shows the western blot results of cell lysates from the purified CD4+ T cells of HIV-infected, non-suppressed patients. CD4+ T cells from an HIV-negative donor was used as a negative control, while HA-TRAIL-s transfected HEK-293T cells were used as a positive control. TRAIL-s expression was higher in HIV-infected CD4+ T cells as compared to CD4+ T cells from an uninfected individual.

Figure 11:
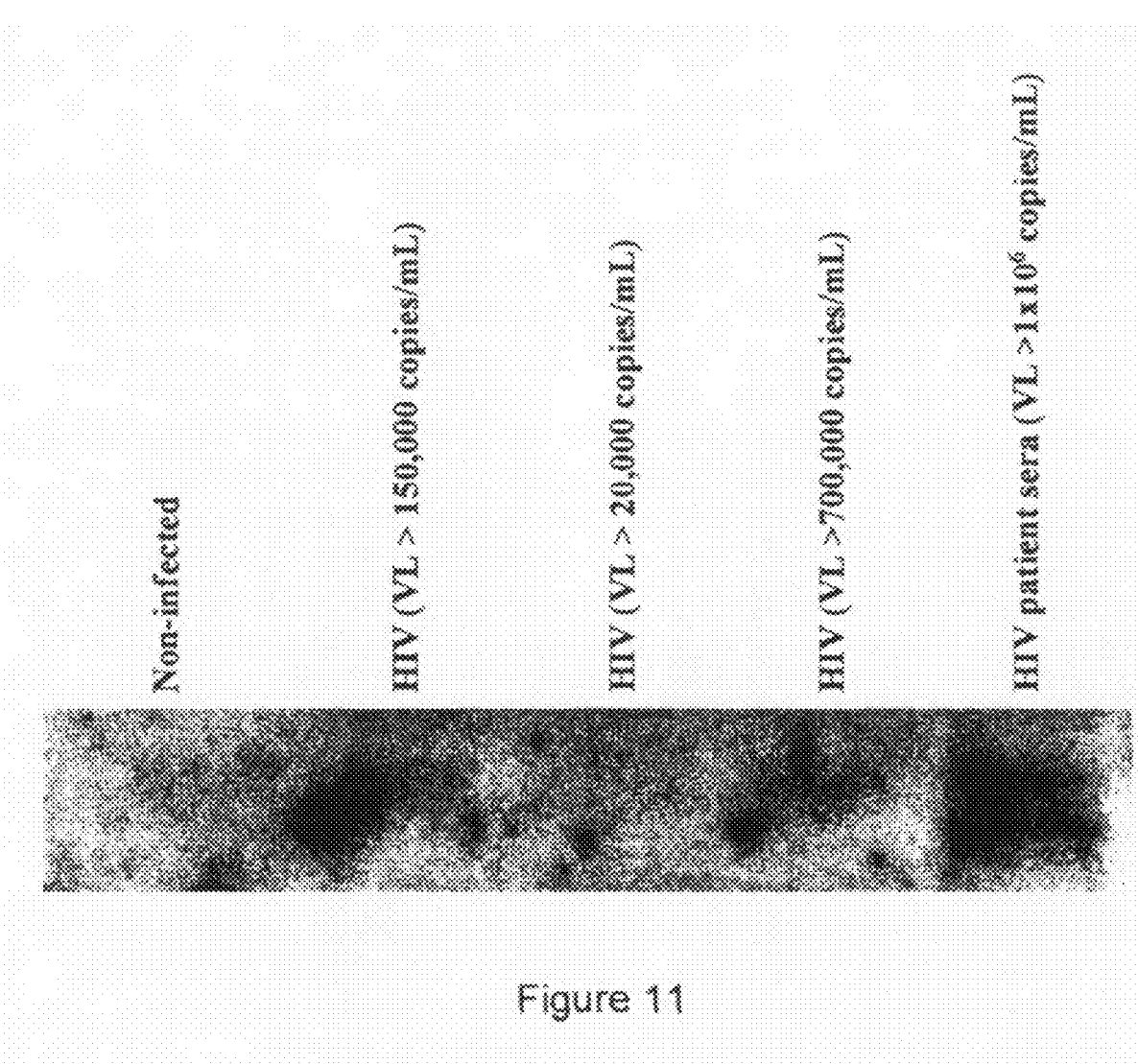
FIG. 11. TRAIL-s in sera from HIV-infected patients. VL indicates viral load.

FIG. 11 shows the immunoprecipitation of TRAIL-s from HIV-infected patient sera. Immunoprecipitation was performed using a chimeric recombinant TRAIL-R2 (DR5)/human Fc protein covalently coupled to sepharose beads. Immunoprecipitated TRAIL-s was detected by Western blotting. Viral loads detected in the plasma of these patients are indicated. These results demonstrate an apparent viral load correlation with TRAIL-s expression.

Figure 12:
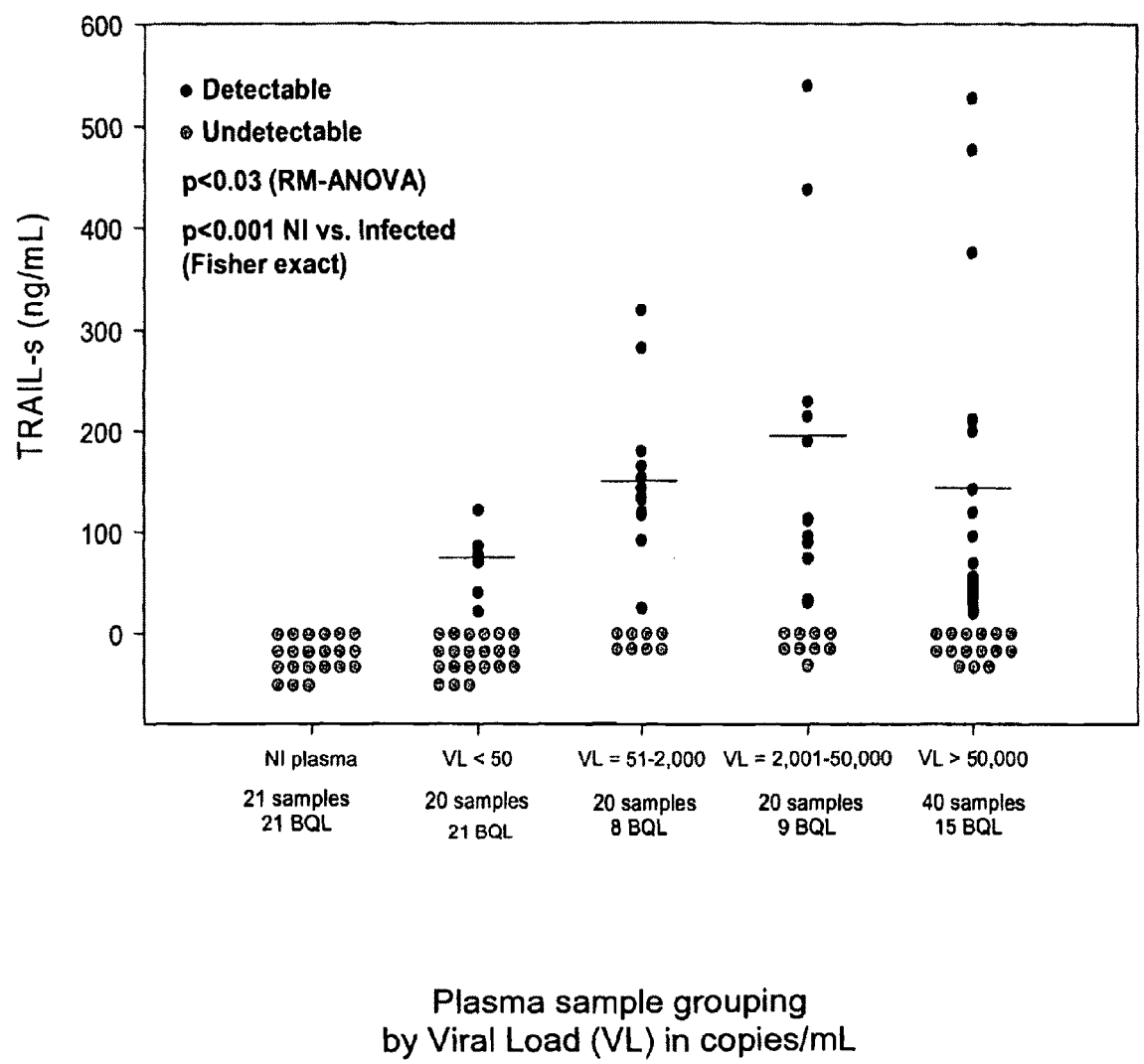
FIG. 12. Quantitation of TRAIL-s concentrations in patient sera using ELISA.

Sandwich immunoassays, using plate-bound chimeric TRAIL-R2/FC polypeptide as the capture reagent and mouse monoclonal antibodies against TRAIL-s as the detection reagent, were performed on HIV patient sera as well as normal human sera to further quantitate the concentrations of TRAIL-s found circulating in HIV patient serum (FIG. 12). The plasma of HIV-infected patients contained up to 500 ng/mL of TRAIL-s, and the presence of TRAIL-s correlated directly with viral replication.

TRAIL-s is Responsible for TRAIL Resistance in Certain Tumors.

Figure 6:
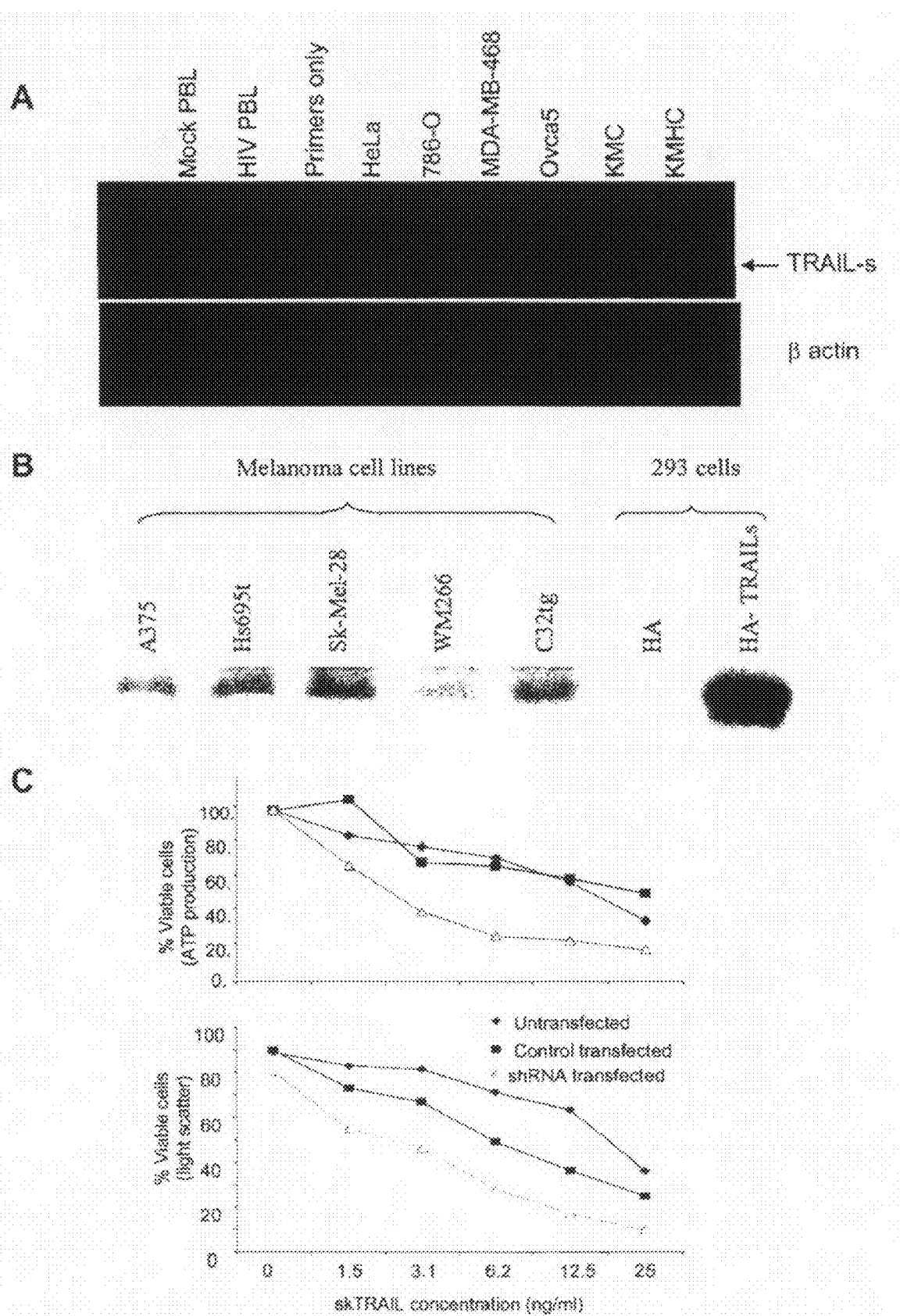
FIG. 6. (A) TRAIL-s expression in tumor cell lines. (B) TRAIL-s expression in melanoma cell lines. (C) MDA-MB-468 cell viability in the presence of skTRAIL tx, after TRAIL-s knockdown with shRNA.

Tumor cell lines were selected based upon their known relative resistance to TRAIL-mediated cell death. These tumors were screened by RT-PCR and by Western blot for the presence of TRAIL-s. Five of twelve tumor cell lines tested expressed detectable message (FIG. 6A) for TRAIL-s. Several additional melanoma cell lines exhibited detectable TRAIL-s (FIG. 6B).

To determine whether the presence of TRAIL-s was responsible for the TRAIL resistance in tumors, MDA-MB-468 cells were stably transfected with an RNAi construct specific for TRAIL-s, for Lamin, or were left untransfected. These cells were treated with 0-25 ng/mL of skTRAIL, and their sensitivity to TRAIL-mediated cell death was assessed. MDA-MB-468 cells expressing a TRAIL-s-specific miRNA were more sensitive to skTRAIL-induced cell death than untransfected or laminin-specific miRNA-transfected cells (FIG. 6C).

Example 2

Evaluating the Role of TRAIL-s on Immunoregulation

TRAIL-s Binding Affinity to TRAIL Receptors

TRAIL-s receptor-binding affinity and real-time binding kinetics are measured using a Biacore surface plasmon resonance instrument. Briefly, recombinantly produced, GST-tagged or biotinylated TRAIL-s is immobilized to the surface of a Biacore CM5 or SA sensor chip and used as bait for serial injections using increasing concentrations of recombinant TRAIL receptor/Fc chimera proteins. Each of the five TRAIL receptors (e.g., TRAIL-R1, -R2, -R3, -R4, and OPG) are tested and their relative association and dissociation constants are calculated for comparisons.

The affinities of each TRAIL receptor for TRAIL-s and for full-length TRAIL are determined using a competition assay, wherein each of the sensor chip-bound recombinant TRAIL receptor/Fc chimera proteins is first saturated with recombinant full-length TRAIL and then is competed off through injections of increasing concentrations of recombinant HA-TRAIL-s. Multiple repetitions of each experiment using regenerated chips, as well as the inverse experiment (i.e., prior saturation with GST-TRAIL-s followed by competition using injections of increasing concentrations of full length TRAIL) provide precise assessment of the relative affinities of TRAIL-s and full length TRAIL for each of the TRAIL receptors. Such experiments also determine whether TRAIL-s is a competitive, non competitive, or mixed inhibitor of TRAIL.

Agents That Induce TRAIL-s Expression

Agents (e.g., growth factors, cytokines, hormones, or chemokines) are tested to determine their ability to induce TRAIL-s expression. Briefly, PBLs are incubated in the presence or absence of agents such as cytokines (e.g., type I and type II interferons), growth factors (e.g., TGF-β), and toll like receptor (e.g., TLR 2, 3, 7, 8, and 9) agonists. Following incubation, cells are lysed and are assessed for TRAIL-s expression by RT-PCR and western blot analysis.

TRAIL-s in T Cell Induced Cytotoxicity

Cells (e.g., T cells, B cells, NK cells, monocytes, macrophages, plasmacytoid dendritic cells) from HIV-infected patients are assessed for the expression of TRAIL-s using Western blot analysis. TRAIL-s expression is confirmed by single cell RT-PCR. Cell types expressing TRAIL-s are subjected to further fractionation. For example, T cells are further fractionated into memory, effector, CD4, and CD8 subsets. Agents that induce the expression of TRAIL-s are further characterized functionally using cytotoxicity assays.

Assessing TRAIL-s Effects on HIV Injection

HIV susceptible cell lines (e.g., Jurkat T cells) are stably transfected with an RNAi construct specific for TRAIL-s that is targeted to the splice junction of exons two and five of TRAIL. Cells expressing a TRAIL-s specific RNAi construct are infected with HIV and assessed for TRAIL sensitivity, HIV virus production, and the presence of chronic HIV infection.

Example 3

Determining the Role of TRAIL-s in the Immuno-Pathogenesis of Melanoma

Correlation of TRAIL-s Expression With Melanoma Parameters

TRAIL-s expression is assessed in the plasma of patients with malignant melanoma and in malignant melanoma tissues using methods such as ELISA and immunohistochemistry. TRAIL-s expression level is correlated with melanoma stage, type, phenotype, and disease outcome.

TRAIL-s in Melanoma Avoidance of CTL-Induced Cell Death

Melanoma cells (e.g., cell lines or primary cells) having reduced levels of TRAIL-s are used as targets in a cytotoxicity assay. TRAIL-s levels can be reduced by, for example, using an antibody that recognizes TRAIL-s or by transfecting melanoma cells with a TRAIL-s-specific RNAi construct. Melanoma cells having normal levels of TRAIL-s and melanoma cells having reduced levels of TRAIL-s are labeled with DiO and are co-incubated with cytotoxic T lymphocytes (CTLs). DiO-labeled melanoma cells are then assessed for apoptosis using flow cytometry. Apoptosis levels in melanoma cells having reduced levels of TRAIL-s can be compared to apoptosis levels in melanoma cells having normal TRAIL-s levels to assess the role of TRAIL-s in melanoma avoidance of CTL-induced cell death.

Melanoma-Specific CTL-Mediated Cell Death

MHC Class 1-deficient T2 target cells are loaded with a melanoma-associated antigen (e.g., a gp100 polypeptide) using standard protocols and are co-cultured with CTLs from melanoma patients in the presence or absence of recombinant TRAIL-s. The level of apoptosis in the T2 target cells is assessed using flow cytometry. Apoptosis levels in cultures incubated in the presence of recombinant TRAIL-s can be compared to apoptosis levels in cultures incubated in the absence of recombinant TRAIL-s to assess the role of TRAIL-s in melanoma-specific CTL-mediated cell death.

Example 4

Evaluating the Role of TRAIL-s in Hepatitis C Virus (HCV) Persistence

Determining the Effect of HCV Polypeptide Expression on TRAIL-s Expression

Human hepatocytes (e.g., the Huh7 cell line or primary hepatocytes) are transfected with an expression vector for one of nine HCV polypeptides, the complete virus, or with an empty vector. The cells are then lysed and assessed for TRAIL-s expression by RT-PCR and Western blot analysis.

Frozen liver samples from HCV-infected patients, from non-infected control patients, and from non-infected non-alcoholic steatohepatitis (NASH) patients (i.e., non-infected inflammatory controls) are also assessed for TRAIL-s expression by RT-PCR and Western blot analysis.

TRAIL-s in Acute HCV Clearance

Blood samples from young intravenous drug users are assessed for TRAIL-s expression using ELISA and Western blot analysis before, during, and after acute HCV infection. TRAIL-s expression can be compared during each stage of infection and between individuals that clear the infection and those that establish persistent infections.

Ex Vivo Clearance of HCV

Hepatocytes from HCV-infected patients are isolated after liver biopsy and digested into a cell suspension using methods described elsewhere (Vlahakis, et al., *J Infect. Dis.*, 188: 1455-1460 (2003)). Peripheral blood is obtained from the patients at the time of liver biopsy, and CD8+ T cells are isolated using Stem Cell enrichment cocktail for humans (StemCells, Inc., Palo Alto, Calif.). The hepatocytes and CD8+ T cells are co-cultured at varying effector to target ratios in the presence or absence of anti-TRAIL antibody or isotype control. The hepatocytes are assessed for apoptosis by flow cytometry and HCV infection. HCV infection in hepatocytes can be assessed by staining the hepatocytes with fluorescently labeled anti-HCV antibodies or isotype control antibodies and analyzing them by flow cytometry. HCV infection can also be assessed by using RT-PCR to amplify a conserved region in the 5' untranslated region of HCV from hepatocyte RNA.

Example 5

Evaluating the Ability of TRAIL-Short to Confer Immune Escape

Figure 13:
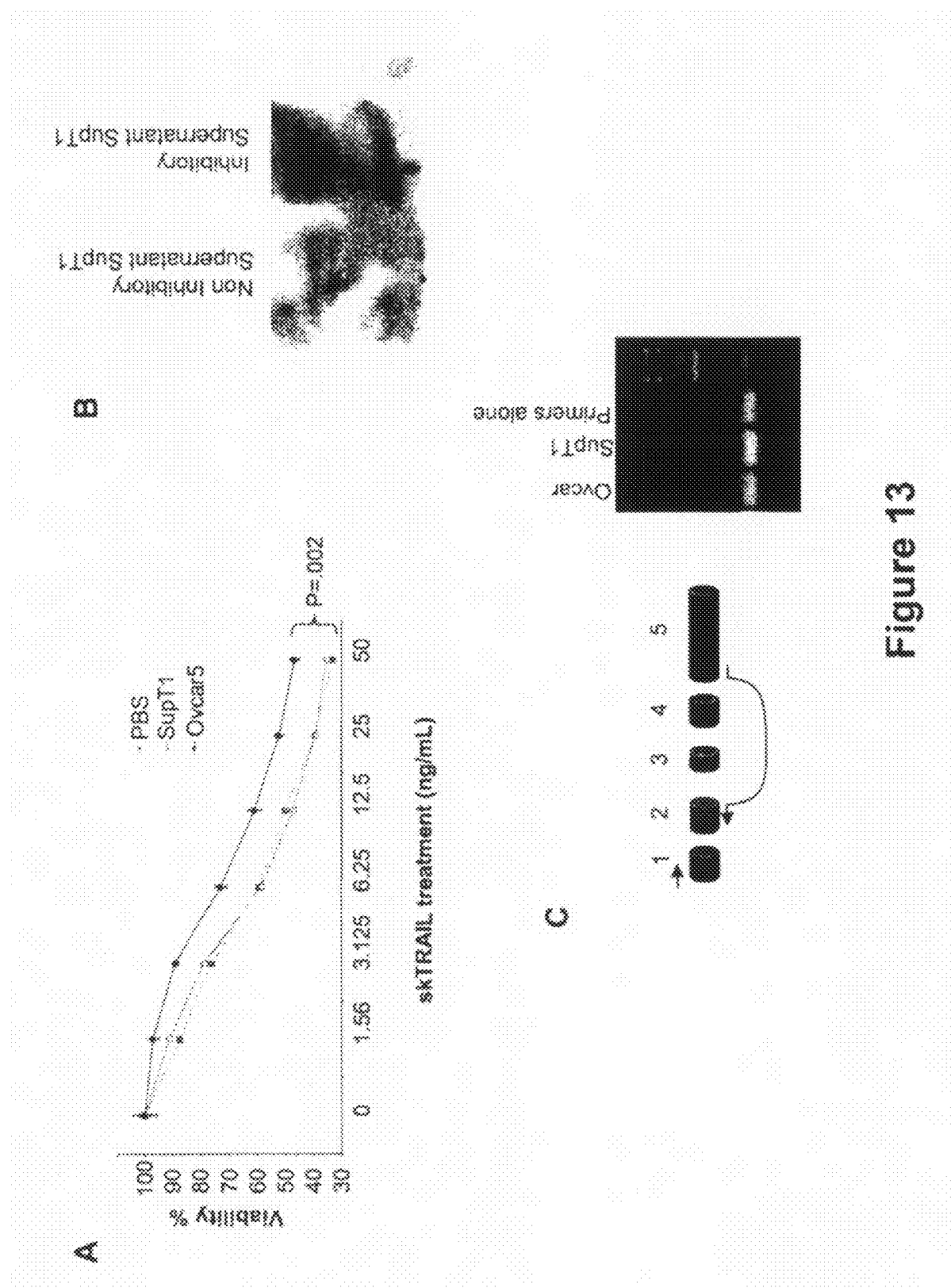
FIG. 13. HIV infection of PBLs increases TRAIL and TRAIL-receptor expression, but TRAIL:TRAIL receptor blockade does not alter HIV-associated cell death. Peripheral blood lymphocytes from HIV-negative donors were infected in vitro with HIV-1 (IIIB) or mock-infected and analyzed 4 days following infection for (A) surface TRAIL receptor expression or (B) surface TRAIL receptor expression. Mock-infected PBLs (light gray histograms), HIV-infected PBLs (dark gray histograms) or isotype (black histograms) are shown. Co-staining for the HIV antigen p24 revealed that the increase in TRAIL expression occurred within the population of PBLs also staining positive for p24 (results representative of four independent experiments). (C) Soluble TRAIL was measured in the culture supernatants of mock- or HIV-infected PBLs. The result shown is the mean of four infections, +/−s.e.m. (D) TRAIL-mediated death in PBL cultures was determined by serial treatment of PBL cultures (mock- and HIV-infected) with an isotype control antibody or neutralizing anti-TRAIL antibody. Independent experiments confirmed the ability of the neutralizing antibody (clone 2E5) to inhibit TRAIL-mediated death in TRAIL-sensitive cells treated with skTRAIL. Data is representative of three separate replicates.

Experiments were performed to determine whether or not TRAIL resistant cells can modify TRAIL sensitivity of bystander cells in a paracrine fashion. The ovarian cancer cell line, Ovcar5, was chosen as a representative TRAIL receptor expressing cell lines that is TRAIL resistant. Ovcar5 cells were incubated at a high density in PBS for one hour. The supernatant was used to pretreat TRAIL-sensitive Jurkat T cells. Treatment of the Jurkat T cells with the supernatant conferred a relative resistance to TRAIL-mediated killing (FIG. 13A). In contrast, supernatants from SupT1 cells, which express TRAIL receptors and are TRAIL sensitive, failed to antagonize Jurkat killing by TRAIL. Moreover, the resistance was TRAIL specific, since Jurkat T cells pretreated with Ovcar5 supernatant were as sensitive to Fas-induced death as were control cells.

Ovcar5 and SupT1 supernatants were immunoblotted with a polyclonal anti-TRAIL antibody. A TRAIL immunoreactive band of 14 kD was observed, which was too short to be either TRAILα, β, or γ (FIG. 13B). The presence of the TRAIL immunoreactive polypeptide was not inhibited by matrix metalloprotease inhibitors, aprotinin, or leupeptin.

To determine whether the TRAIL immunoreactive band might be TRAIL-s, combinations of sense and antisense primers from each exon were used to perform RT-PCR. Performing RT-PCR with a sense primer from exon 1 (SEQ ID NO:6) and an antisense primer from exon 5 (SEQ ID NO:11), amplified a product having a sequence that suggested exons 3 and 4 were excised. Performing RT-PCR with a sense primer from exon 1 (SEQ ID NO:6) and an antisense primer spanning exons 2 and 5 (SEQ ID NO:18) amplified TRAIL-s in Ovcar5, but not SupT1 cells (FIG. 13C).

TRAIL-s Binds TRAIL Receptor 2

As described in Example 1, experiments were performed which demonstrated that TRAIL-s binds to TRAIL receptor 2. The ability of TRAIL-s to bind TRAIL receptor 2 (also termed Death Receptor 5, or DR5) was confirmed using a pull-down approach, and was then applied to samples of interest in order to demonstrate the presence of TRAIL-s. Briefly, 100 nanograms of a recombinant chimeric polypeptide consisting of the extracellular portion of TRAIL-R2 linked by a peptide spacer to a human immunoglobulin Fc domain (R&D Systems, Minneapolis, Minn.) was incubated with sample and 50 μL of a 50-50 slurry of Protein A/G-agarose beads (Santa Cruz Biotechnology, Santa Cruz, Calif.) in a volume sufficient to allow mixing. The mixture was incubated at 4° C. overnight on a rotator. The beads were pelleted, washed gently with PBS, and boiled in Lamellae sample buffer before loading on a 15% SDS-polyacrylamide gel. After electrophoresis, polypeptides were transferred to Immobilon-P membranes (Millipore, Billerica, Mass.). Western blotting of the membranes was performed as described herein.

Figure 14:
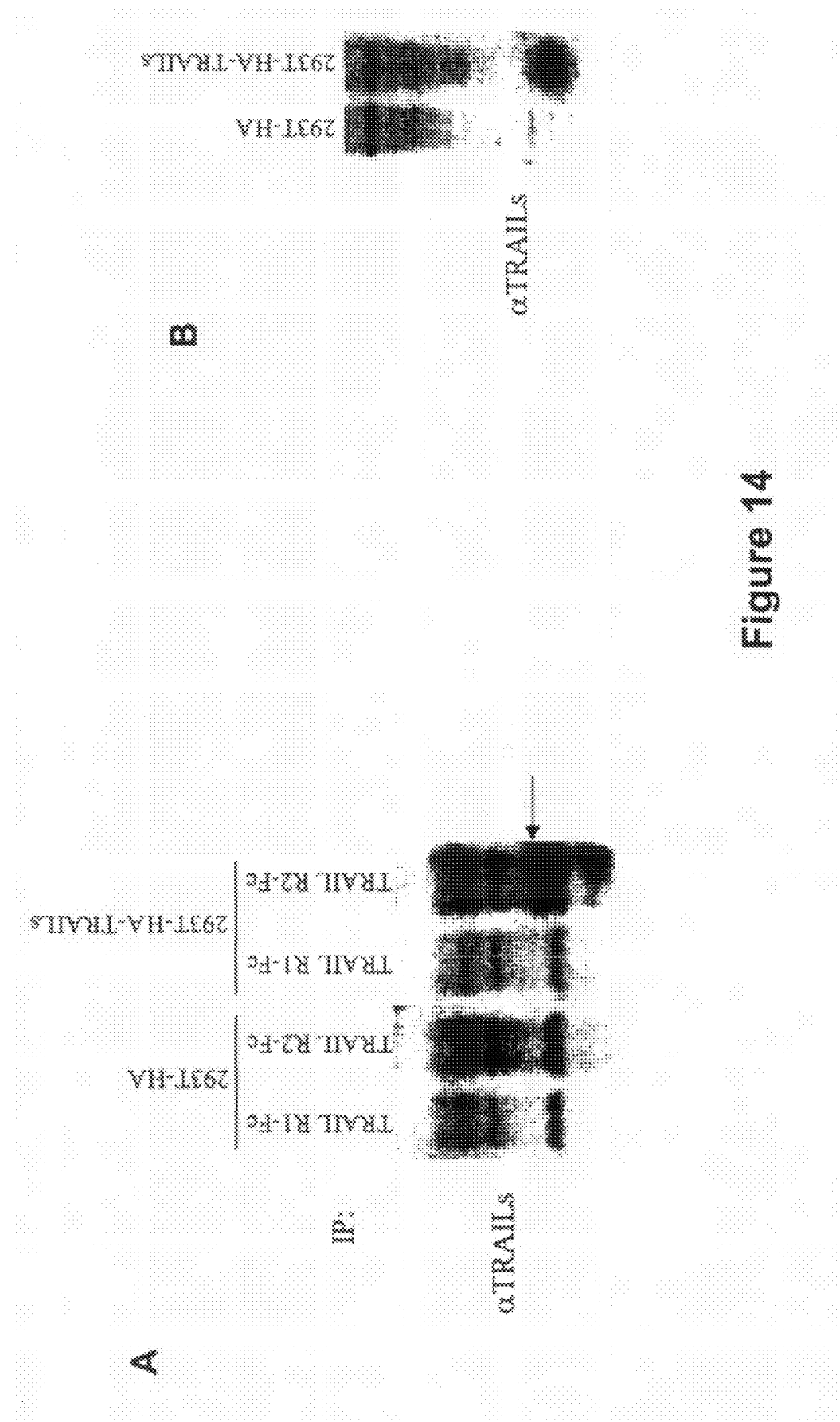
FIG. 14. (A) Immunoprecipitation of TRAIL-s with TRAIL R2-Fc fusion protein. TRAIL R1-Fc or TRAIL R2-Fc fusion proteins were used to perform immunoprecipitations using lysates from 293T cells that were transfected with constructs containing nucleic acids encoding HA or HA-TRAIL-s. (B) Western blot analysis of lysates from 293T cells transfected with constructs containing nucleic acids encoding HA or HA-TRAIL-s. The blot was probed using an anti-TRAIL-s monoclonal antibody.

Immunoprecipitation using TRAIL-R1 or -R2 Fc demonstrated that TRAIL-R2, but not TRAIL-R1, interacted with TRAIL-s (FIG. 14A), as detected using a monoclonal antibody specific for TRAIL-s (FIG. 14B).

TRAIL-s Inhibits Apoptosis and is the TRAIL Inhibitor Produced by Ovcar5

Figure 15:
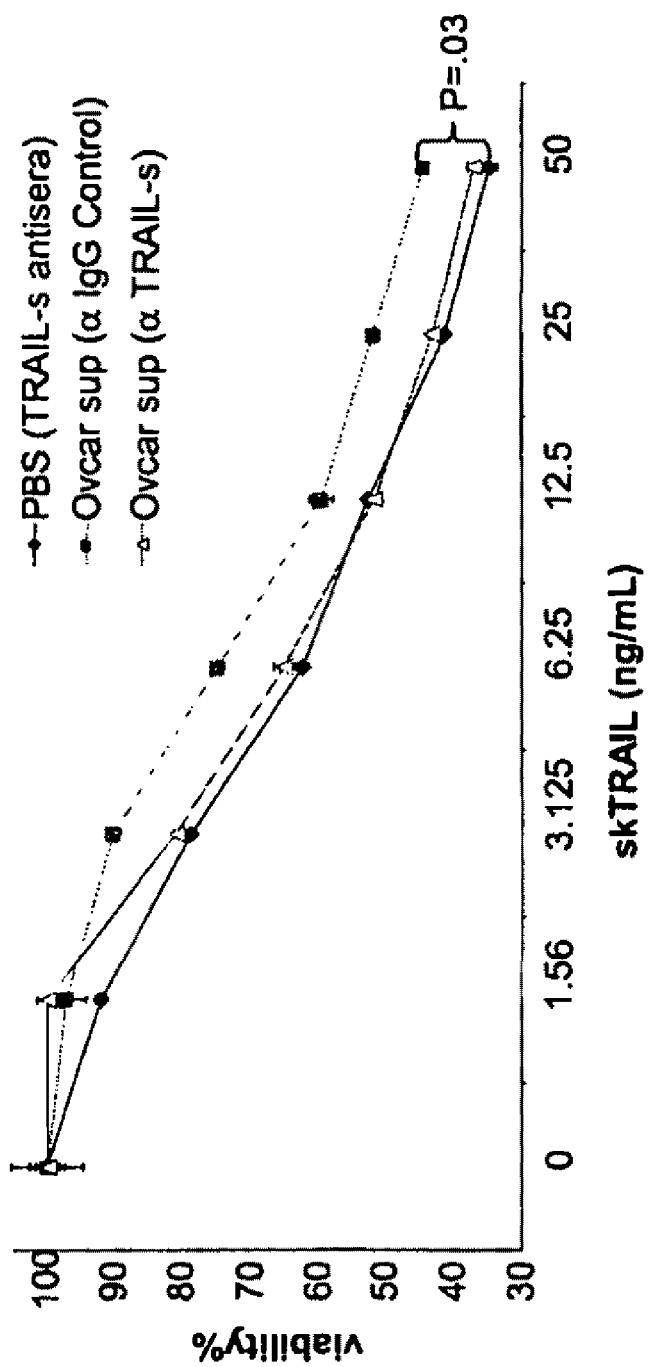
FIG. 15. Viability of Jurkat T cells treated with the indicated concentrations of skTRAIL following pretreatment with PBS, with anti-TRAIL-s antibodies, or with supernatant from Ovcar5 cells that was immunodepleted with anti-TRAIL-s antibodies or control antibodies (α IgG Control).

Experiments were performed to determine whether immunodepletion of TRAIL-s alters the ability of Ovcar5 supernatants to inhibit TRAIL-induced death. Untreated supernatant from Ovcar5 cells inhibited skTRAIL-induced killing of Jurkat T cells. Similarly, supernatant from Ovcar5 cells immunodepleted with control antibody maintained antagonistic activity against skTRAIL killing (FIG. 15). However, when the supernatant was immunodepleted using anti-TRAIL-s antibody, the antagonism of the supernatant against TRAIL-induced killing was lost (FIG. 15). These results demonstrated that TRAIL-s was the factor contained within supernatants from Ovcar5 cells that caused resistance to TRAIL-mediated killing.

TRAIL-s Confers Resistance to Antigen-Specific CTL Killing

Figure 16:
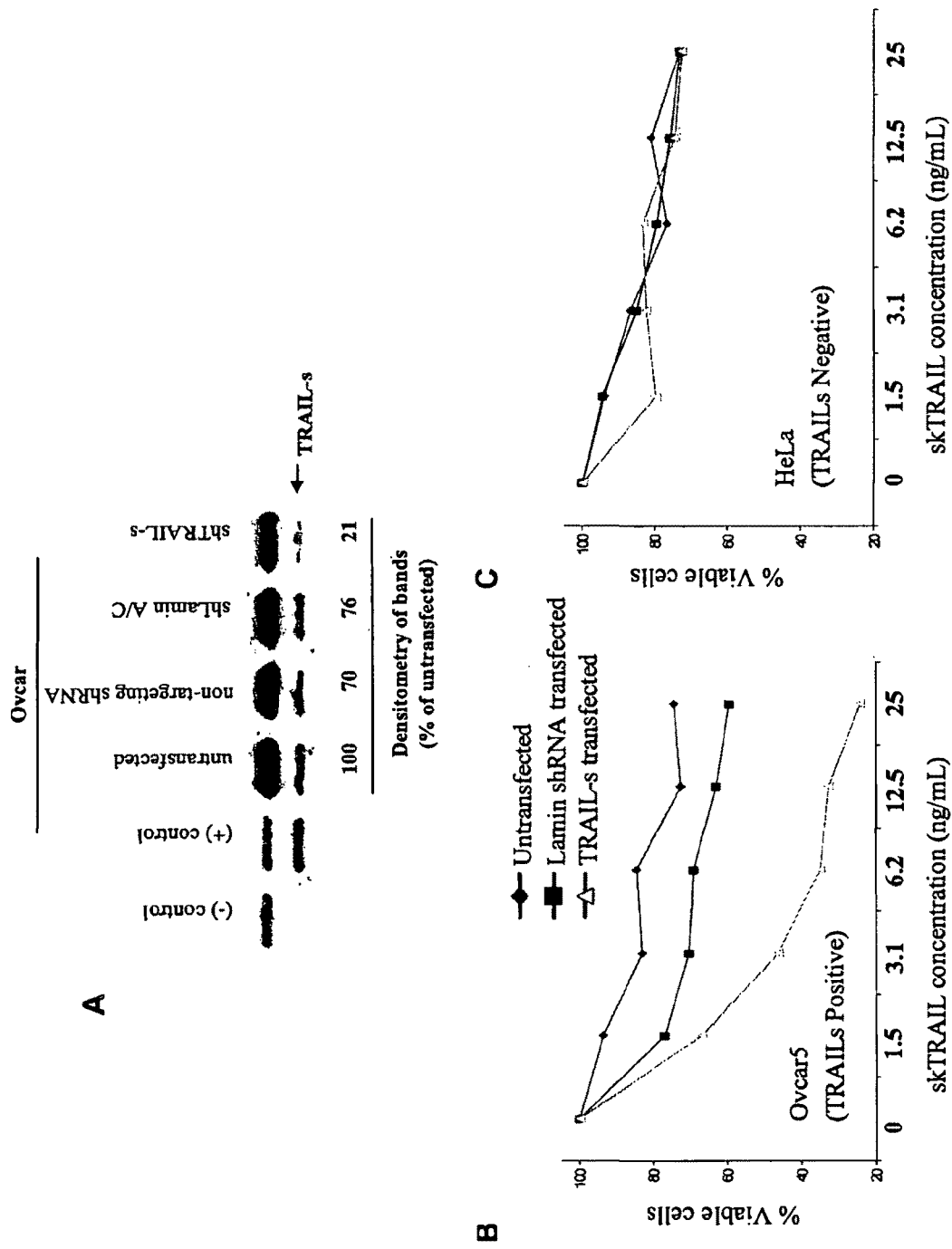
FIG. 16. (A) Western blot demonstrating RNAi knockdown of TRAIL-s. The blot was probed using anti-TRAIL-s antisera 48 hours post-transfection of a representative TRAIL-s expressing cancer line, Ovcar5, with shRNA oligos targeting the TRAIL-s splice variant. (B) Viability of Ovcar5 cells in the presence of the indicated concentrations of skTRAIL. The Ovcar5 cells were untransfected or transfected with control shRNA (Lamin shRNA) or shRNA targeted to TRAIL-s. (C) Viability of HeLa cells in the presence of the indicated concentrations of skTRAIL. The HeLa cells were untransfected or transfected with control shRNA or shRNA targeted to TRAIL-s (see legend for FIG. 16B).

Ovcar5 cells were stably transfected with shRNA specific for TRAIL-s, Lamin, or empty vector (FIG. 16B), and protein knockdown was confirmed by Western blot (FIG. 16A). RNAi knockdown of TRAIL-s was accomplished through transfection of shRNA oligos targeting the splice variant. Protein knockdown was assessed by Western blotting 48 hours post-transfection, using anti-TRAIL-s antisera. The transfectants were treated with a range of skTRAIL concentrations, and their sensitivity to TRAIL-mediated killing was determined. Ovcar5 cells demonstrated a significant increase in skTRAIL sensitivity upon knockdown of TRAIL-s, whereas introduction of the same shRNA constructs into HeLa cells (which do not express TRAIL-s) did not alter TRAIL sensitivity (FIG. 16C).

Figure 17:
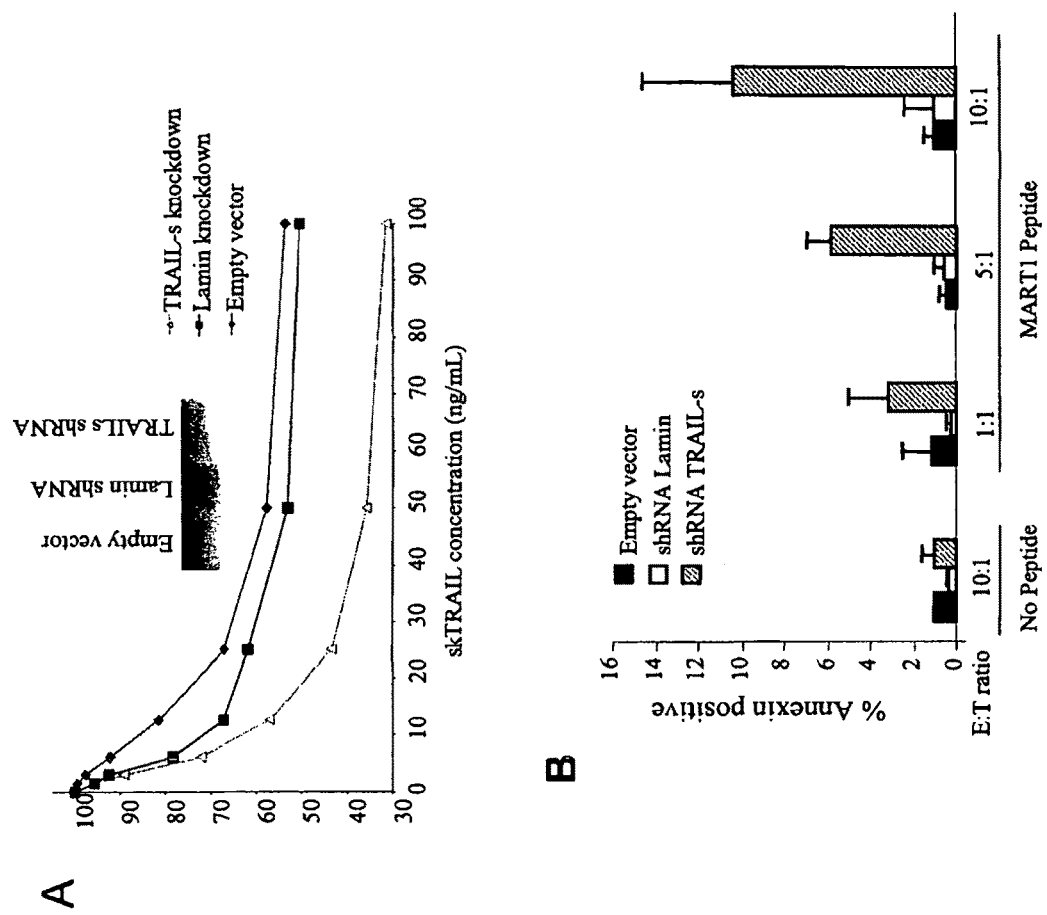
FIG. 17. (A) Viability of A375 cells in the presence of the indicated concentrations of skTRAIL. The A375 cells were untransfected or transfected with control shRNA or shRNA targeted to TRAIL-s. (B) Cytotoxicity assays performed using a cloned MART 1 specific CTL against melanoma targets with or without TRAIL-s knockdown. A375 target cells were loaded with MART 1 peptide, and CTL killing of target cells was compared in cells without peptide loading and in target cells preloaded with MART 1 peptide.

To determine whether melanoma cell lines express TRAIL-s polypeptide, Western blotting was performed as described in Example 1 (FIG. 6B) shRNA was then used to knock down TRAIL-s expression in the melanoma cell line A375. Knockdown of TRAIL-s expression in the melanoma cells was observed to enhance TRAIL sensitivity (FIG. 17A). These results indicate that resistance of melanoma cells to TRAIL is mediated by TRAIL-s.

MART 1 is an immunodominant HLA A2 restricted melanoma epitope. CTLs from HLA A2 positive patients with stage IV disease were assessed for MART 1 specificity and for TRAIL co-expression. Patients' PBLs were observed to contain a significant proportion of MART1 specific CTLs, the majority of which expressed TRAIL. These results indicate that melanoma specific CTLs express TRAIL, and melanoma cells express TRAIL receptors. Due to the presence of TRAIL-s, however, melanoma cells are TRAIL resistant. The presence of TRAIL-s may be responsible for CTL resistance in melanoma cells.

Despite a high frequency of MART 1 specific CTLs, these cells exhibit minimal cytolytic activity against melanoma targets in vitro and in vivo. To directly assess whether TRAIL-s is responsible, cytotoxicity assays were performed using a cloned MART 1 specific CTL against the melanoma targets with or without TRAIL-s knockdown. A375 target cells were loaded with MART 1 peptide, and CTL killing of target cells was compared in cells without peptide loading and in target cells preloaded with MART 1 peptide. The CTL clone failed to kill target cells without peptide, MART 1 loaded target cells, MART 1 loaded target cells transfected with empty vector, or MART 1 loaded target cells with knockdown of Laminin. Strikingly, however, killing of target cells loaded with MART 1 and exhibiting TRAIL-s knockdown by CTLs occurred in a significant and dose-responsive manner (FIG. 17B).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal in need of reduced TRAIL-induced apoptosis, said method comprising administering to said mammal an effective amount of a substantially pure polypeptide comprising the sequence set forth in SEQ ID NO:1.

2. The method of claim 1, wherein said mammal is a human.

* * * * *

SEQUENCE LISTING

```
<160> NUMBER OF SEQ ID NOS: 21

<210> SEQ ID NO 1
<211> LENGTH: 101
<212> TYPE: PRT
<213> ORGANISM: Homo sapiens

<400> SEQUENCE: 1

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Thr Pro Arg Met Lys Arg
                85                  90                  95

Leu Trp Ala Ala Lys
            100

<210> SEQ ID NO 2
<211> LENGTH: 11
<212> TYPE: PRT
<213> ORGANISM: Homo sapiens

<400> SEQUENCE: 2

Thr Pro Arg Met Lys Arg Leu Trp Ala Ala Lys
1               5                   10

<210> SEQ ID NO 3
<211> LENGTH: 1776
<212> TYPE: DNA
<213> ORGANISM: Homo sapiens

<400> SEQUENCE: 3
tttcatttcc tcactgacta taaaagaata gagaaggaag ggcttcagtg accggctgcc      60
tggctgactt acagcagtca gactctgaca ggatcatggc tatgatggag gtccaggggg     120
gacccagcct gggacagacc tgcgtgctga tcgtgatctt cacagtgctc ctgcagtctc     180
tctgtgtggc tgtaacttac gtgtacttta ccaacgagct gaagcagatg caggacaagt     240
```

```
actccaaaag tggcattgct tgtttcttaa aagaagatga cagttattgg gaccccaatg      300
acgaagagag tatgaacagc ccctgctggc aagtcaagtg caactccgt cagctcgtta       360
gaaagatgat tttgagaacc tctgaggaaa ccatttctac agttcaagaa aagcaacaaa      420
atatttctcc cctagtgaga gaaagaggtc ctcagagagt agcagctcac ataactggga      480
ccagaggaag aagcaacaca ttgtcttctc caaactccaa gaatgaaaag gctctgggcc      540
gcaaaataaa ctcctgggaa tcatcaagga gtgggcattc attcctgagc aacttgcact      600
tgaggaatgg tgaactggtc atccatgaaa aagggtttta ctacatctat tcccaaacat      660
actttcgatt tcaggaggaa ataaagaaa cacaaagaa cgacaaacaa atggtccaat        720
atatttacaa atacacaagt tatcctgacc ctatattgtt gatgaaaagt gctagaaata      780
gttgttggtc taaagatgca gaatatgac tctattccat ctatcaaggg ggaatatttg       840
agcttaagga aaatgacaga attttttgttt ctgtaacaaa tgagcacttg atagacatgg     900
accatgaagc cagtttttttc ggggcctttt tagttggcta actgacctgg aaagaaaaag    960
caataacctc aaagtgacta ttcagttttc aggatgatac actatgaaga tgtttcaaaa    1020
aatctgacca aaacaaacaa acagaaaaca gaaaacaaaa aaacctctat gcaatctgag    1080
tagagcagcc acaaccaaaa aattctacaa cacacactgt tctgaaagtg actcacttat    1140
cccaagagaa tgaaattgct gaaagatctt tcaggactct acctcatatc agtttgctag    1200
cagaaatcta gaagactgtc agcttccaaa cattaatgca atggttaaca tcttctgtct    1260
ttataatcta ctccttgtaa agactgtaga agaaagagca acaatccatc tctcaagtag    1320
tgtatcacag tagtagcctc caggtttcct taagggacaa catccttaag tcaaaagaga    1380
gaagaggcac cactaaaaga tcgcagtttg cctggtgcag tggctcacac ctgtaatccc    1440
aacattttgg gaacccaagg tgggtagatc acgagatcaa gagatcaaga ccatagtgac    1500
caacatagtg aaaccccatc tctactgaaa gtacaaaaat tagctgggtg tgttggcaca    1560
tgcctgtagt cccagctact tgagaggctg aggcaagaga attgtttgaa cccgggaggc    1620
agaggttgca gtgtggtgag atcatgccac tacactccag cctggcgaca gagcgagact    1680
tggtttcaaa aaaaaaaaaa aaaaaaactt cagtaagtac gtgttatttt tttcaataaa    1740
attctattac agtatgtcaa aaaaaaaaaa aaaaaa                               1776
```

<210> SEQ ID NO 4
<211> LENGTH: 306
<212> TYPE: DNA
<213> ORGANISM: Homo sapiens

<400> SEQUENCE: 4

```
atggctatga tggaggtcca gggggaccc agcctgggac agacctgcgt gctgatcgtg       60
atcttcacag tgctcctgca gtctctctgt gtggctgtaa cttacgtgta ctttaccaac     120
gagctgaagc agatgcagga caagtactcc aaaagtggca ttgcttgttt cttaaaagaa     180
gatgacagtt attgggaccc caatgacgaa gagagtatga acagcccctg ctggcaagtc     240
aagtggcaac tccgtcagct cgttagaaag actccaagaa tgaaaaggct ctgggccgca    300
aaataa                                                                306
```

<210> SEQ ID NO 5
<211> LENGTH: 36
<212> TYPE: DNA
<213> ORGANISM: Homo sapiens

<400> SEQUENCE: 5

```
actccaagaa tgaaaaggct ctgggccgca aaataa                                    36

<210> SEQ ID NO 6
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 6
tctgacagga tcatggctat g                                                    21

<210> SEQ ID NO 7
<211> LENGTH: 17
<212> TYPE: DNA
<213> ORGANISM: Artificial Sequence
<220> FEATURE:
<223> OTHER INFORMATION: synthetically generated oligonucleotide

<400> SEQUENCE: 7
cagcctggga cagacct                                                         17

<210> SEQ ID NO 8
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 8
caggacaagt actccaaaag t                                                    21

<210> SEQ ID NO 9
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 9
tgagaacctc tgaggaaacc                                                      20

<210> SEQ ID NO 10
<211> LENGTH: 23
<212> TYPE: DNA
<213> ORGANISM: Artificial Sequence
<220> FEATURE:
<223> OTHER INFORMATION: synthetically generated oligonucleotide

<400> SEQUENCE: 10
agcaacaaaa tatttctccc cta                                                  23

<210> SEQ ID NO 11
<211> LENGTH: 19
<212> TYPE: DNA
<213> ORGANISM: Artificial Sequence
<220> FEATURE:
<223> OTHER INFORMATION: synthetically generated oligonucleotide

<400> SEQUENCE: 11
actaaaaagg ccccgaaaa                                                       19

<210> SEQ ID NO 12
<211> LENGTH: 19
<212> TYPE: DNA
<213> ORGANISM: Artificial Sequence
<220> FEATURE:
```

```
<223> OTHER INFORMATION: synthetically generated oligonucleotide

<400> SEQUENCE: 12
cctctggtcc cagttatgt                                               19

<210> SEQ ID NO 13
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 13
tggtttcctc agaggttctc                                              20

<210> SEQ ID NO 14
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 14
acggagttgc cacttgactt                                              20

<210> SEQ ID NO 15
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 15
gaaactacct tcaactccat c                                            21

<210> SEQ ID NO 16
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 16
cgaggccagg atggagccgc c                                            21

<210> SEQ ID NO 17
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 17
cggatccatg gctatgatgg                                              20

<210> SEQ ID NO 18
<211> LENGTH: 41
<212> TYPE: DNA
<213> ORGANISM: Artificial Sequence
<220> FEATURE:
<223> OTHER INFORMATION: synthetically generated oligonucleotide

<400> SEQUENCE: 18
ttattttgcg gcccagagcc ttttcattct tggagtcttt c                      41

<210> SEQ ID NO 19
```

```
<211> LENGTH: 12
<212> TYPE: PRT
<213> ORGANISM: Artificial Sequence
<220> FEATURE:
<223> OTHER INFORMATION: synthetic peptide

<400> SEQUENCE: 19

Cys Thr Pro Arg Met Lys Arg Leu Trp Ala Ala Lys
 1               5                  10

<210> SEQ ID NO 20
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 20
aagacccttg tgctcgttgt c                                                  21

<210> SEQ ID NO 21
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 21
aaaacactag ttctagtagt c                                                  21
```